(12) United States Patent
Centeno et al.

(10) Patent No.: US 12,233,188 B2
(45) Date of Patent: Feb. 25, 2025

(54) BONE MARROW ADIPOSE PORTION ISOLATION DEVICE AND METHODS

(71) Applicant: Regenexx, LLC, Des Moines, IA (US)

(72) Inventors: Christopher Centeno, Broomfield, CO (US); Ryan Dregalla, Broomfield, CO (US); Nicolette Lyons, Broomfield, CO (US); Patrick Reischling, Broomfield, CO (US)

(73) Assignee: Regenexx, LLC, Des Moines, IA (US)

( * ) Notice: Subject to any disclaimer, the term of this patent is extended or adjusted under 35 U.S.C. 154(b) by 0 days.

(21) Appl. No.: 17/569,738

(22) Filed: Jan. 6, 2022

(65) Prior Publication Data

US 2022/0184135 A1 Jun. 16, 2022

Related U.S. Application Data

(60) Continuation of application No. 16/730,408, filed on Dec. 30, 2019, now abandoned, which is a
(Continued)

(51) Int. Cl.
*A61M 1/02* (2006.01)
*A61K 35/28* (2015.01)
(Continued)

(52) U.S. Cl.
CPC .......... *A61M 1/029* (2013.01); *A61K 35/28* (2013.01); *A61M 1/3693* (2013.01);
(Continued)

(58) Field of Classification Search
CPC ..... A61K 35/28; A61M 1/029; A61M 1/3693; A61M 2202/08; A61M 2202/10; B01D 21/26; B01D 21/262; B01L 3/50215; B01L 2200/025; B01L 2300/044; B01L 2300/0861; B01L 2300/0864; B01L 2400/0409; B04B 7/08; C12M 33/04; C12M 45/04; C12N 5/0663;
(Continued)

(56) References Cited

U.S. PATENT DOCUMENTS

| 6,398,972 B1 | 6/2002 | Blasetti et al. |
| 2006/0094865 A1 | 5/2006 | Kapur |

(Continued)

FOREIGN PATENT DOCUMENTS

| KR | 10-2011-0079122 | 7/2011 |
| WO | WO 2013-066013 | 5/2013 |
| WO | WO 2015-021189 | 2/2015 |

OTHER PUBLICATIONS

International Search Report and Written Opinion dated Nov. 19, 2014 for International Patent Application No. PCT/US2014/049992.
(Continued)

*Primary Examiner* — John Kim
(74) *Attorney, Agent, or Firm* — Quarles & Brady LLP

(57) ABSTRACT

The embodiments disclosed herein generally relate to systems, devices and methods for the fractionation, isolation, extraction and processing of the adipose supernatant layer of a bone marrow aspirate. In particular, the various embodiments relate to systems, devices, and methods of obtaining, utilizing, and processing the adipose supernatant layer of a bone marrow aspirate as a source of mesenchymal stem cells.

14 Claims, 24 Drawing Sheets

Related U.S. Application Data continuation of application No. 15/958,940, filed on Apr. 20, 2018, now Pat. No. 10,537,596, which is a division of application No. 14/778,530, filed as application No. PCT/US2014/049992 on Aug. 6, 2014, now Pat. No. 9,976,115.

(60) Provisional application No. 61/862,837, filed on Aug. 6, 2013.

(51) Int. Cl.

| | | |
|---|---|---|
| *A61M 1/36* | (2006.01) | |
| *B01D 21/26* | (2006.01) | |
| *B01L 3/00* | (2006.01) | |
| *B04B 7/08* | (2006.01) | |
| *C12M 1/00* | (2006.01) | |
| *C12M 1/26* | (2006.01) | |
| *C12N 5/077* | (2010.01) | |
| *C12N 5/0775* | (2010.01) | |
| *G01N 33/49* | (2006.01) | |
| *G01N 33/68* | (2006.01) | |

(52) U.S. Cl.
CPC ........... *B01D 21/26* (2013.01); *B01D 21/262* (2013.01); *B01L 3/50215* (2013.01); *B04B 7/08* (2013.01); *C12M 33/04* (2013.01); *C12M 45/04* (2013.01); *C12N 5/0663* (2013.01); *C12N 5/0667* (2013.01); *C12N 5/0669* (2013.01); *G01N 33/491* (2013.01); *G01N 33/6872* (2013.01); *A61M 2202/08* (2013.01); *A61M 2202/10* (2013.01); *B01L 2200/025* (2013.01); *B01L 2300/044* (2013.01); *B01L 2300/0861* (2013.01); *B01L 2300/0864* (2013.01); *B01L 2400/0409* (2013.01)

(58) Field of Classification Search
CPC .. C12N 5/0667; C12N 5/0669; G01N 33/491; G01N 33/6872; A61P 43/00
See application file for complete search history.

(56) References Cited

U.S. PATENT DOCUMENTS

| | | |
|---|---|---|
| 2006/0251628 A1 | 11/2006 | Attawia |
| 2006/0278588 A1 | 12/2006 | Woodell-May |
| 2010/0256595 A1 | 10/2010 | Leach et al. |
| 2010/0260721 A1 | 10/2010 | McGonaigie |
| 2011/0036786 A1 | 2/2011 | Ellsworth |
| 2016/0298076 A1 | 10/2016 | Centeno et al. |
| 2018/0305655 A1 | 10/2018 | Centeno et al. |

OTHER PUBLICATIONS

European Search Report, dated Feb. 3, 2017, 11 pages.
U.S. Appl. No. 14/778,530, Office Action-Restriction-Requirement, dated Jun. 23, 2017, 7 pages.
U.S. Appl. No. 14/778,530, Non-Final Office Action dated Sep. 13, 2017, 16 pages.
U.S. Appl. No. 14/778,530, Notice of Allowance, dated Apr. 4, 2018, 16 pages.
European Examination Report, EU Patent Application No. 14834894.9 dated Apr. 9, 2019; 4 pages.
Insausti et al., Stem Cells and Development, vol. 21, No. 2, pp. 260-272 (2012).
Notice of Allowance, U.S. Appl. No. 15/958,940, dated Sep. 30, 2019.

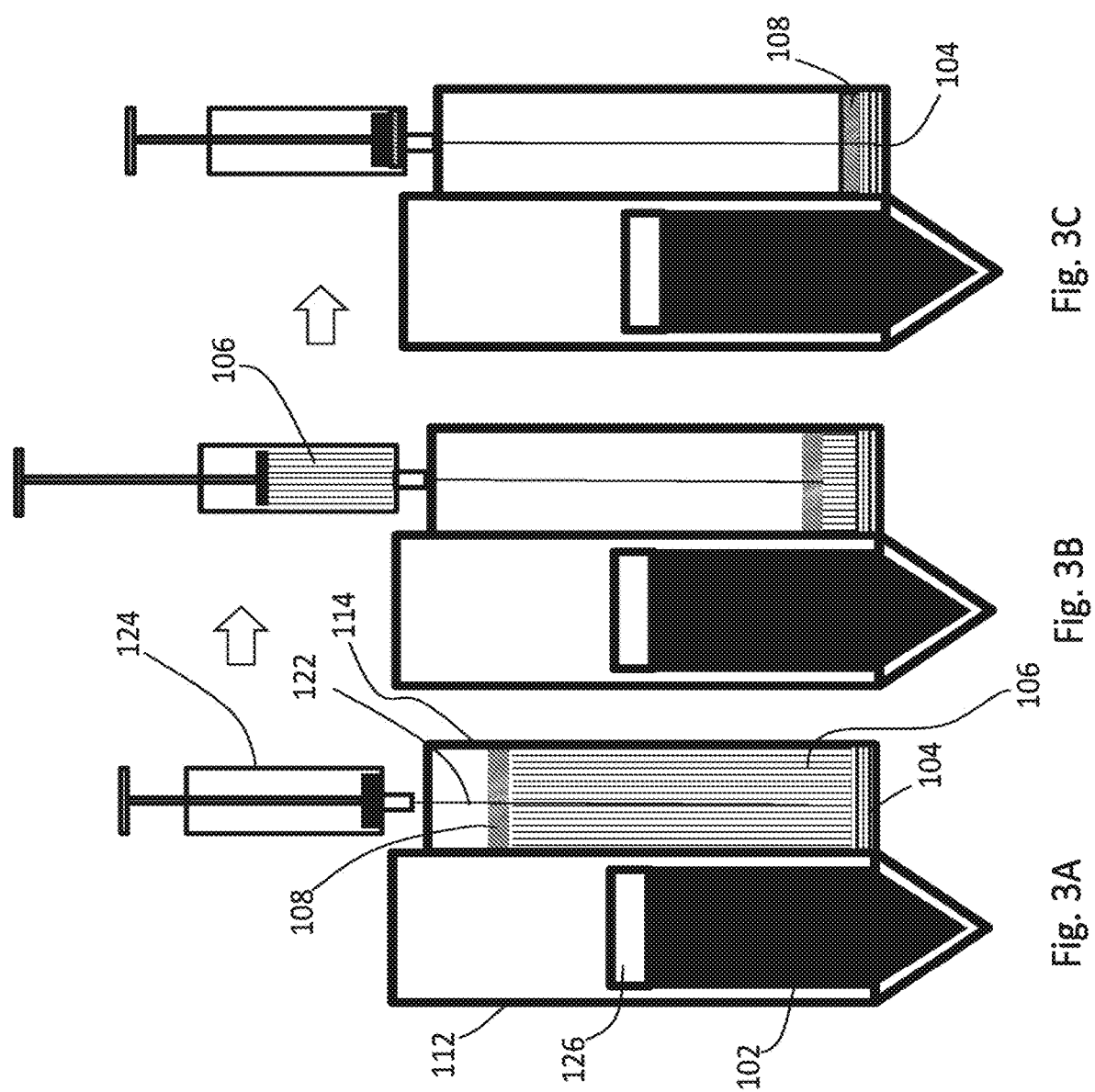

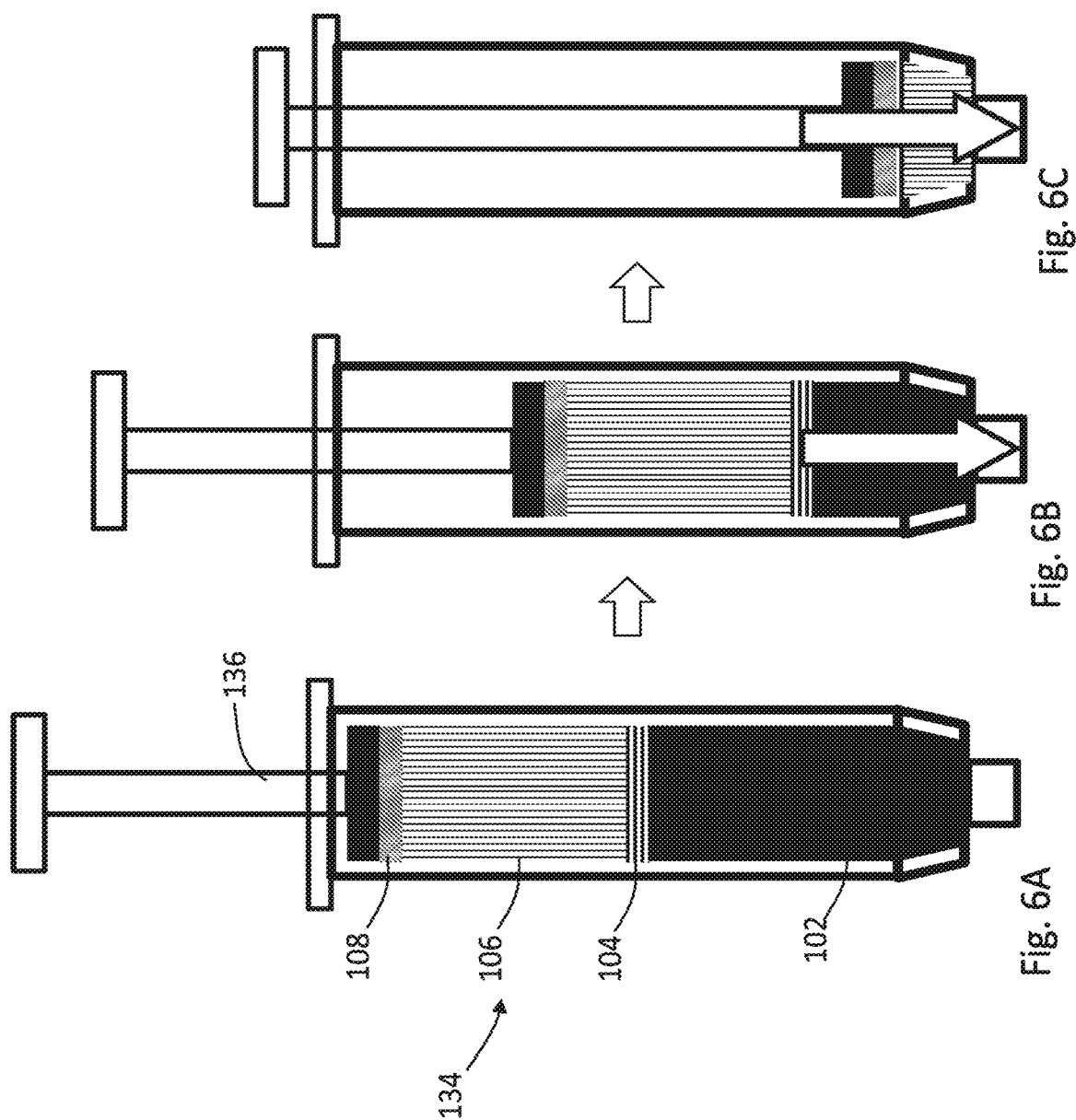

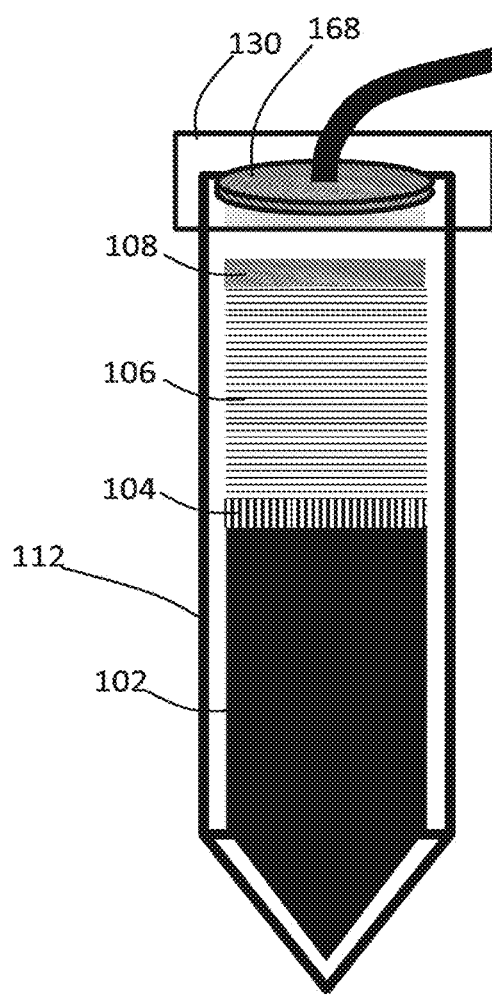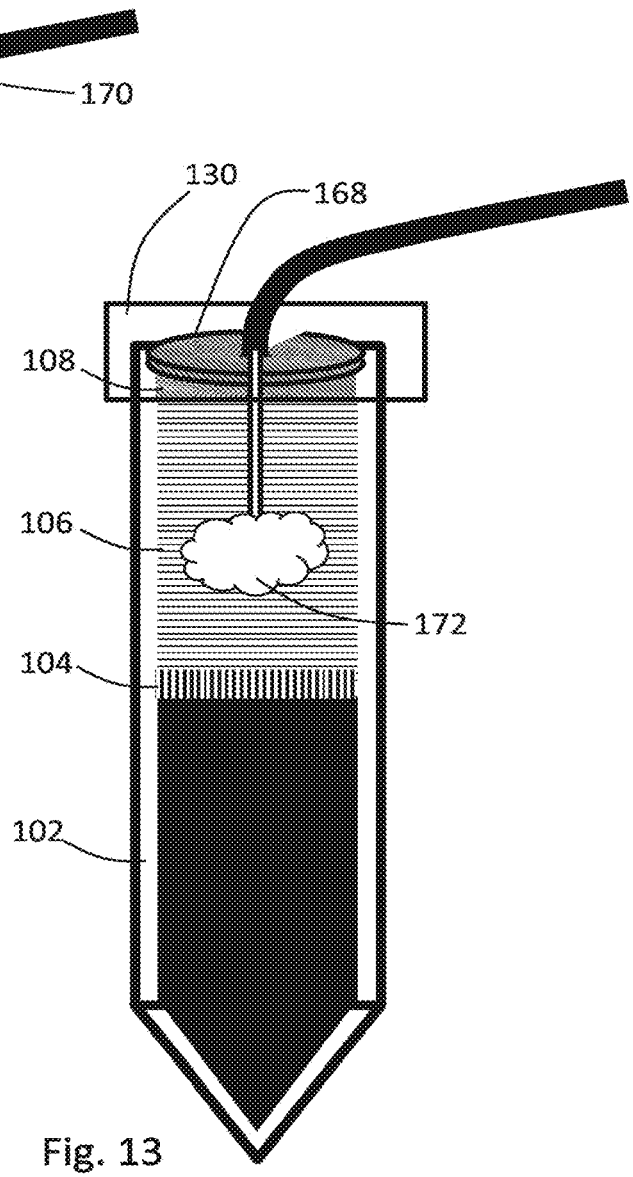
Fig. 12
Fig. 13

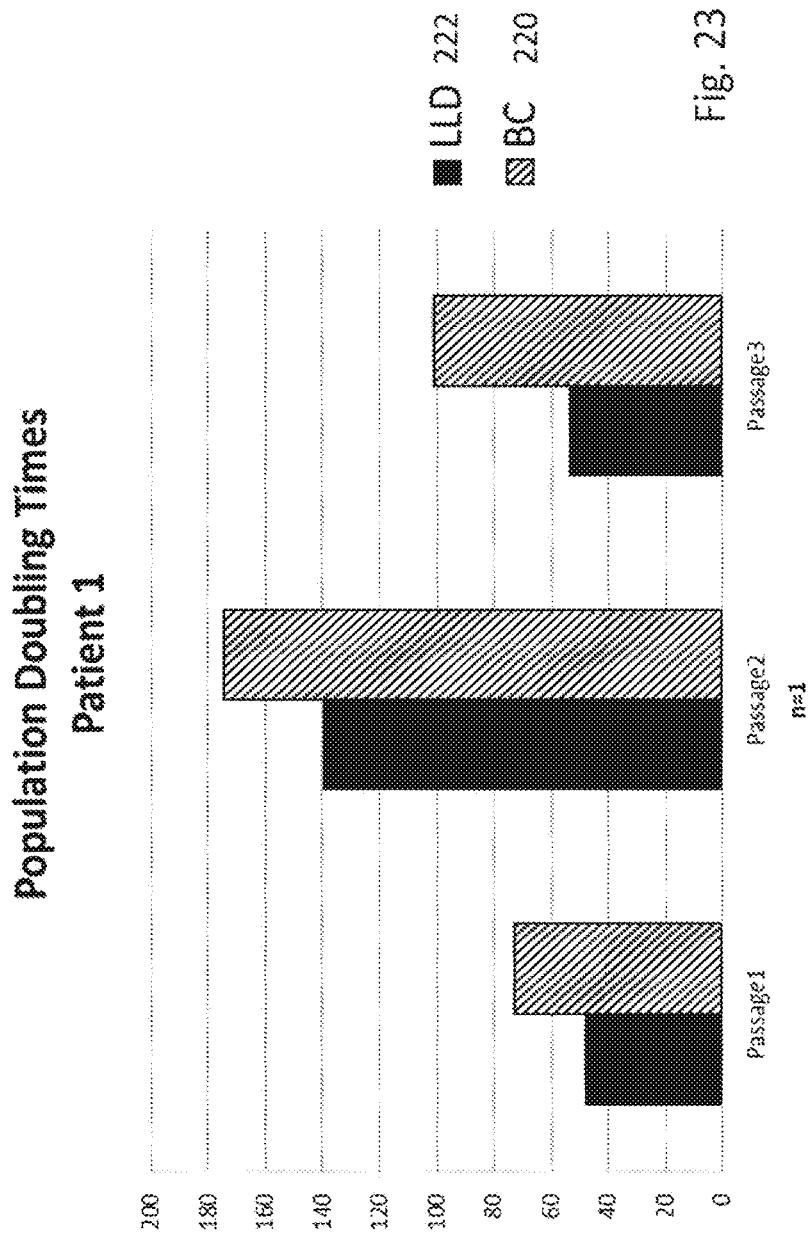

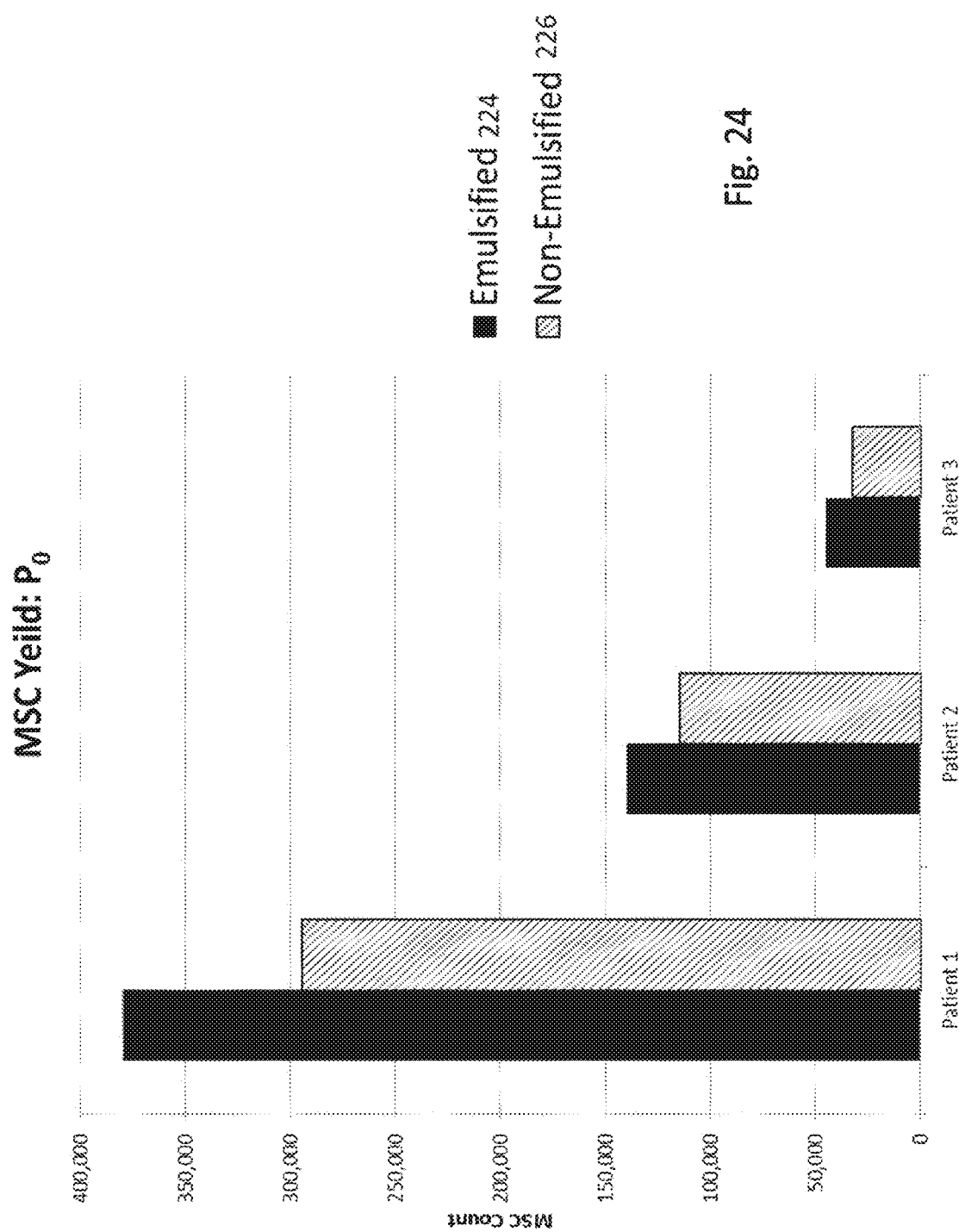

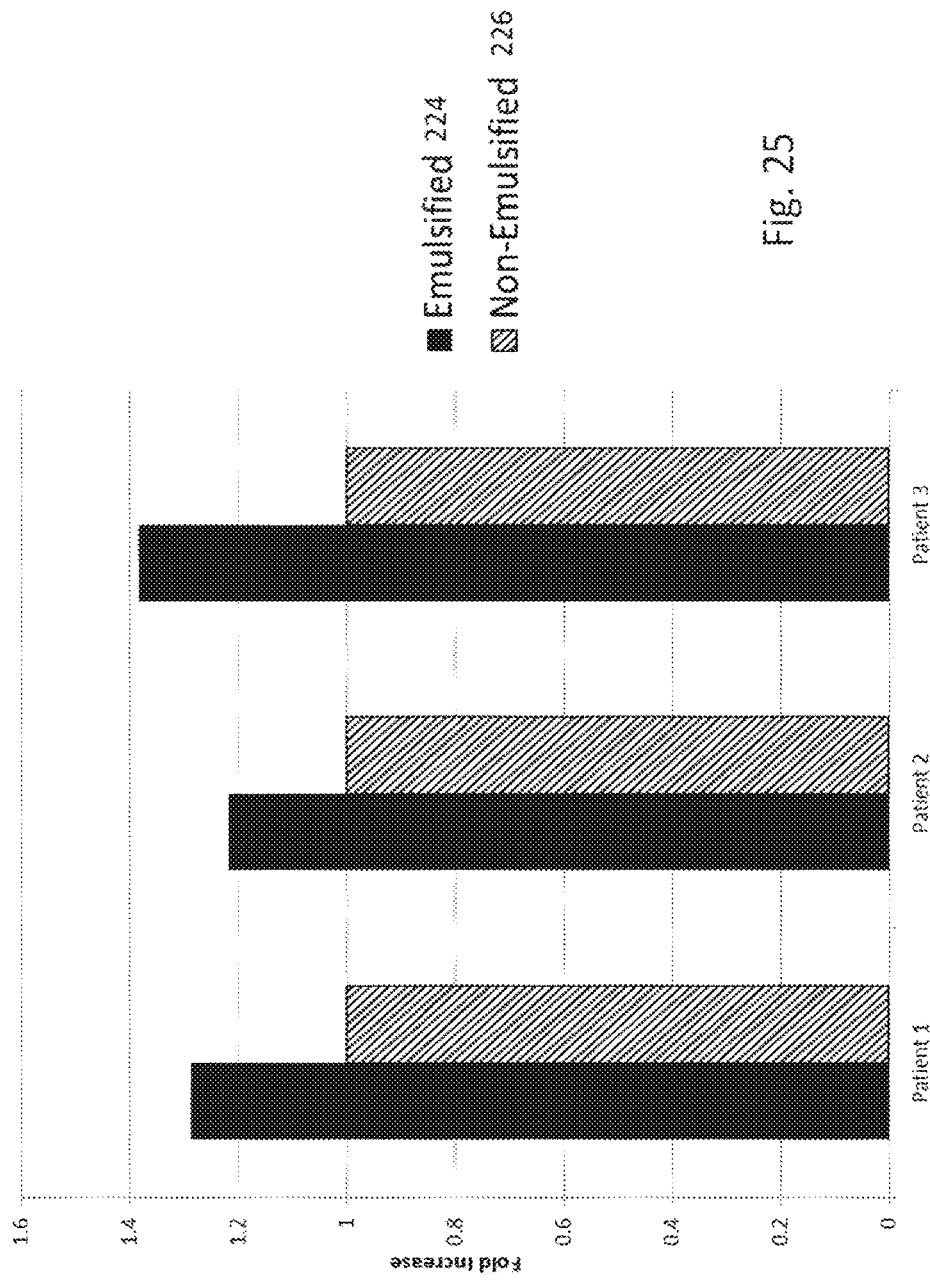

BONE MARROW ADIPOSE PORTION ISOLATION DEVICE AND METHODS

RELATED APPLICATIONS

This application is a continuation of U.S. application Ser. No. 16/730,408 filed on Dec. 30, 2019, now abandoned, entitled "Bone Marrow Adipose Portion Isolation Device and Methods", which is a continuation of U.S. application Ser. No. 15/958,940 filed on Apr. 20, 2018, now U.S. Pat. No. 10,537,596, entitled "Bone Marrow Adipose Portion Isolation Device and Methods", which is a divisional of U.S. application Ser. No. 14/778,530, filed on Sep. 18, 2015, now U.S. Pat. No. 9,976,115, entitled "Bone Marrow Adipose Portion Isolation Device and Methods", which is a 35 U.S.C. § 371 national phase application of PCT/US14/49992 (WO 2015/021189), filed on Aug. 6, 2014, entitled "Bone Marrow Adipose Portion Isolation Device and Methods", which application claims the benefit of U.S. Provisional Application Ser. No. 61/862,837, filed Aug. 6, 2013, which is incorporated herein by reference in its entirety.

BACKGROUND

Adult mesenchymal stem cells (MSCs) are capable of robust tissue repair. MSCs can be isolated from many autologous tissue sources with the two most common sources being adipose tissue and bone marrow. Adipose stem cell harvesting is performed through liposuction of subcutaneous fat tissue which is then usually processed with a chemical digestion technique. Bone marrow aspirate is a red liquid when first obtained from the patient through a trocar inserted through the bony cortex. The aspirate fluid is then typically processed with centrifugation to separate out various marrow fractions (referred to herein as fractions or layers). The buffy coat is a middle fraction of centrifuged marrow, positioned below a serum component and above a red blood cell component. The buffy coat is rich in nucleated cells, progenitor cells, and stem cells.

Until recently, only the buffy coat of a fractionated bone marrow aspirate was known to include useful quantities of MSCs. Accordingly, typical bone marrow fractionation and concentration systems designed to isolate a therapeutically significant quantity of MSCs have focused on isolating and processing the buffy coat through various means. Conventional methods and devices do not provide for the isolation or subsequent processing of other marrow fractions that are now known to contain MSCs, in particular a marrow adipose layer supernatant which is positioned above the serum layer when bone marrow aspirate is fractionated. Therefore, according to conventional techniques, the marrow adipose supernatant layer is discarded as waste.

Although the adipose layer supernatant of fractionated bone marrow aspirate is now known to include MSCs, no techniques are known for efficiently collecting the adipose layer supernatant and processing same to maximize a useable MSC yield.

The embodiments disclosed herein are directed toward overcoming one or more of the problems discussed above.

SUMMARY OF THE EMBODIMENTS

The embodiments disclosed herein generally relate to systems, devices and methods for the fractionation, isolation, extraction and processing of the adipose supernatant layer of a bone marrow aspirate. In particular, the various embodiments relate to systems, devices and methods of obtaining, utilizing and processing the adipose supernatant layer of a bone marrow aspirate as a source of mesenchymal stem cells.

One embodiment is a method of processing bone marrow aspirate utilizing a device having a first chamber, a second chamber in fluid communication with the first chamber, and a mechanical emulsification system in fluid communication with the second chamber. The method includes fractionating bone marrow aspirate within the first chamber of the device into layers including an adipose layer supernatant. The adipose layer supernatant is collected from the processed bone marrow aspirate in the second chamber. In addition, the adipose layer supernatant is emulsified in the emulsification system.

Method embodiments may further include processing the adipose layer supernatant to collect mesenchymal stem cells. In certain instances, a secondary substance will be added to the bone marrow aspirate. Secondary substances may be, for example, a biologically inert fluid, $CaCl_2$, thrombin, a clotting agent or a polymerization agent. Alternatively, a digestion agent may be added to the collected adipose layer supernatant. A digestion agent may be added separately or, in conjunction with another secondary substance. Representative digestion agents include collagenase or lecithin.

In certain embodiments, the method further includes applying at least one of sonic energy or vibration to the adipose layer supernatant.

The second chamber may be a chamber of any type, including but not limited to, a syringe, pipette or tube in fluid communication with the adipose layer supernatant. The first chamber may also be a chamber of any type, and may include supplemental structures including but not limited to, a cap having a fluid access port providing for the second chamber to be placed into fluid communication with the adipose layer supernatant; a plunger providing for the expulsion of a selected portion of the fractionated bone marrow aspirate from the first chamber; a disk shaped volume which provides for the collection of an adipose layer supernatant fraction at a central region of the disk shaped volume upon the rotation of the first chamber around a central axis; a portion of restricted diameter positioned to correspond with the location of an adipose layer supernatant fraction upon fractionation of bone marrow aspirate placed within the first chamber; a floating disk having a density selected to cause the disk to float substantially between a serum layer and an adipose layer supernatant fraction upon fractionation of the bone marrow aspirate; a porous lipophilic membrane providing for the separation of an adipose layer supernatant fraction upon fractionation of the bone marrow aspirate; or one or more ports in fluid communication with an adipose layer supernatant fraction upon fractionation of the bone marrow aspirate.

The mechanical emulsification system may, in some embodiments, include a first emulsification chamber and a second emulsification chamber in fluid communication with each other through an aperture sized to provide emulsification upon passage of the adipose layer supernatant between the first and second emulsification chambers. Alternatively, the mechanical emulsification system may include a first emulsification chamber and a second emulsification chamber in fluid communication with each other through an emulsification screen providing for the emulsification of the adipose layer supernatant upon passage of adipose layer supernatant between the first and second emulsification chambers. Alternatively, the mechanical emulsification system may include an emulsification screen movable with respect to the adipose layer and providing for the emulsification of the adipose layer supernatant.

BRIEF DESCRIPTION OF THE DRAWINGS

FIGS. 3A, 3B, and 3C are schematic diagrams of another embodiment of device useful for the collection, isolation and/or processing of the adipose supernatant layer of a bone marrow aspirate.

FIGS. 6A, 6B, and 6C are schematic diagrams of another embodiment of device useful for the collection, isolation and/or processing of the adipose supernatant layer of a bone marrow aspirate.

FIG. 12 is a schematic diagram of another embodiment of device useful for the collection, isolation and/or processing of the adipose supernatant layer of a bone marrow aspirate.

FIG. 13 is a schematic diagram of another embodiment of device useful for the collection, isolation and/or processing of the adipose supernatant layer of a bone marrow aspirate.

FIG. 23 is a graphic representation of MSC population doubling times for adipose and buffy coat MSCs derived from 10c.c. bone marrow.

FIG. 24 is a graphic representation of increased PoMSC yield comparing emulsified and non-emulsified samples obtained from the same patient.

FIG. 25 is a graphic representation of increased MSC yield comparing emulsified and non-emulsified samples obtained from the same patient.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
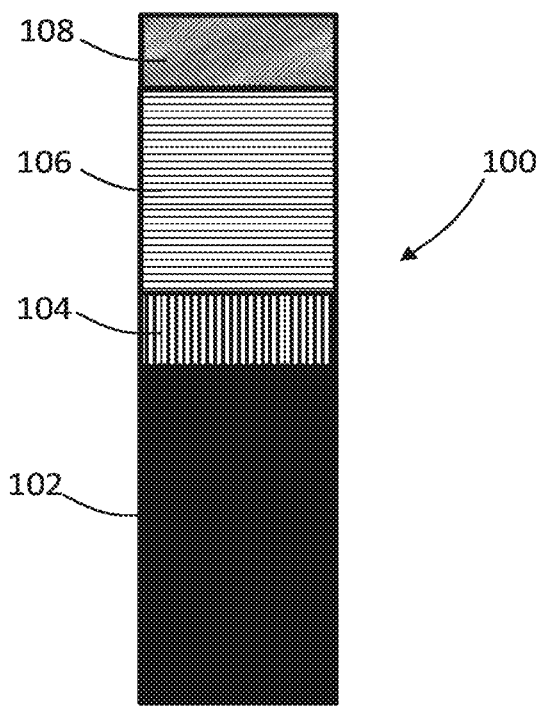
FIG. 1 is a schematic diagram showing selected layers present in fractionated bone marrow aspirate.

Mesenchymal stem cells (MSCs) can be obtained from fractionated bone marrow aspirate. Bone marrow aspirate may be fractionated using a centrifuge-based or similar technique which separates the aspirated fluid into density graded layers. As shown in FIG. 1, fractionated bone marrow aspirate 100 typically includes at least the following layers, ordered from greater to lesser density, a red blood cell (RBC) layer 102, a buffy coat layer 104, a serum layer 106 and an adipose supernatant layer 108. Conventional techniques for the extraction of MSCs from bone marrow aspirates typically feature the isolation and processing of the buffy coat layer 104. Many different methods have been used to isolate the buffy coat. Conventional buffy coat isolation and processing methods discard the adipose layer supernatant 108.

C. L. Insausti, M. B. Blanquer, L. M. Olmo, M. C. Lopez-Martinez, X. F. Ruiz, F. J. Lozano, V. C. Perianes, C. Funes, F. J. Nicolas, M. J. Majado, and J. M. Jimenez, 'Isolation and Characterization of Mesenchymal Stem Cells from the Fat Layer on the Density Gradient Separated Bone Marrow', *Stem Cells Dev*, 21 (2012), 260-72. (Insausti) first disclosed in 2012 that the adipose layer of fractionated bone marrow aspirate contains MSCs. It was estimated by Insausti that processing the adipose layer along with the buffy coat might increase stem cell yields from a bone marrow draw by as much as approximately 50%. The methods and apparatus disclosed herein may be used to isolate, collect and process the adipose layer 108 of fractionated bone marrow aspirate, with or without co-processing of the buffy coat. Alternatively, the apparatus and methods disclosed herein may be used to obtain MSCs from other non-marrow sources of adipose tissue. Surprisingly and advantageously, applicants have demonstrated MSC yields from the adipose layer of bone marrow aspirate which are increased in an amount significantly greater than 50% when compared to the MSC yield obtained when processing the buffy coat alone.

As noted above, Insausti estimated that processing the adipose layer along with the buffy coat might increase stem cell yields from a bone marrow draw by as much as approximately 50%. This relatively modest yield was in part caused by difficulty encountered in extracting the MSCs from the surrounding adipose tissue. In particular, applicants believe that the MSCs in the adipose layer supernatant 108 of fractionated marrow aspirate (or the MSC's in other adipose tissue) may be locked in a fine collagen matrix. For example, abdominal subcutaneous fat has a strong collagen matrix that must be disrupted with chemical digestion before viable stem cells can be obtained. Applicants have determined that mechanical emulsification of the adipose fraction of bone marrow aspirate can greatly increase the MSC yield to values significantly above the 50% increase estimated by Insausti.

Specifically, as detailed below, the novel step of applying mechanical emulsification to adipose layer supernatant resulted in an increased MSC yield by approximately 700%. Applicants believe that the increased MSC yield when compared to Insausti et. al. is due to the mechanical dissociation of stem cells from the finer collagen matrix of this tissue.

Accordingly, the present disclosure provides device embodiments, systems and methods for isolating the stem cell rich adipose layer supernatant 108 (alternatively referred to herein as the adipose LS 108) of whole bone marrow aspirate. Embodiments may optionally include isolating and co-processing the buffy coat layer 104. Embodies may also be applied, in certain instances, to other sources of adipose tissue.

One family of system embodiments feature a closed system suitable for use in a physician's office for the withdrawal of marrow from a patient followed by the substantially contemporaneous rapid isolation of the adipose LS 108 and re-injection or surgical placement of adipose LS 108 or MSCs isolated therefrom into the patient to enhance tissue repair. In another family of embodiments the system may be open ended or partially open ended such that adipose LS or MSCs isolated therefrom are expanded or otherwise processed before reintroduced into the patient to achieve therapeutic goals.

Device embodiments may be used to isolate adipose LS 108 alone or in combination with the buffy coat 104 of a whole marrow aspirate. Device embodiments may also combine the adipose LS 108 with one or more components of the bone marrow aspirate such as the serum layer 106, an isolated fraction of the serum layer and/or buffy coat 104 and/or RBC layer 102 such as platelets or white blood cells.

Method embodiments may be performed manually or automatically or semi-automatically with appropriate devices. Accordingly, certain automated devices incorporate optical sensors or other detectors to identify the various marrow fractions of interest such as the adipose LS 108, serum 106, buffy coat 104, or RBC layer 102.

Figure 2A:
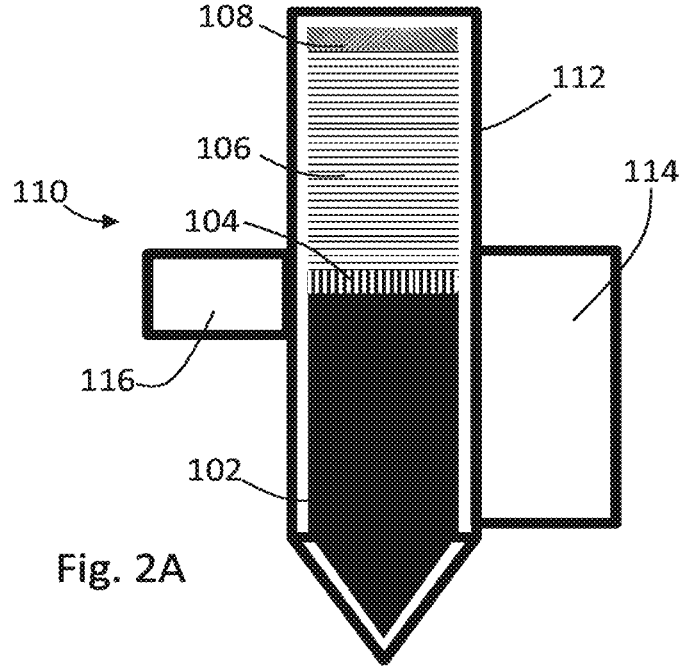
FIGS. 2A, 2B, and 2C are schematic diagrams of one embodiment of device useful for the collection, isolation and/or processing of the adipose supernatant layer of a bone marrow aspirate.

In one specific device embodiment, as shown in FIG. 2A, a centrifuge tube 110 fabricated to have multiple chambers as described below is centrifuged at 100-500 g for 5-10 minutes. The centrifuge tube 110 is provided with a plurality of chambers. The first chamber 112 performs as a typical centrifuge chamber to produce the fractionated bone marrow aspirate with the adipose LS on top 108, the serum layer 106 below the adipose LS, the buffy coat 104 below the serum layer, and the RBC layer 102 below the buffy coat. The centrifuge tube 110 also includes at least a secondary chamber 114 and a tertiary chamber 116 which, for example, provide for the serum layer 106 to be decanted into the secondary chamber 114 and the adipose LS 108 to be collected into the tertiary chamber 116.

Figure 2B:
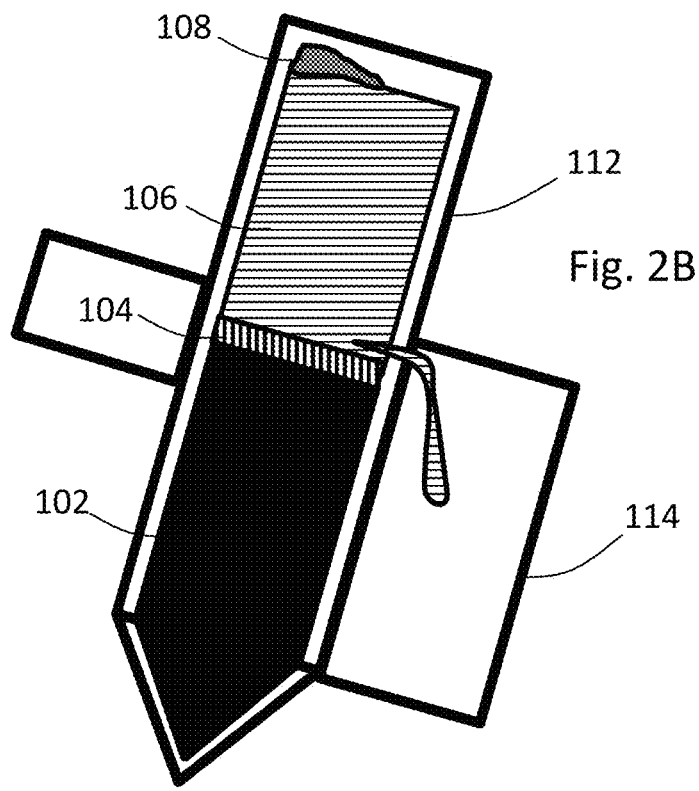
Figure 2C:
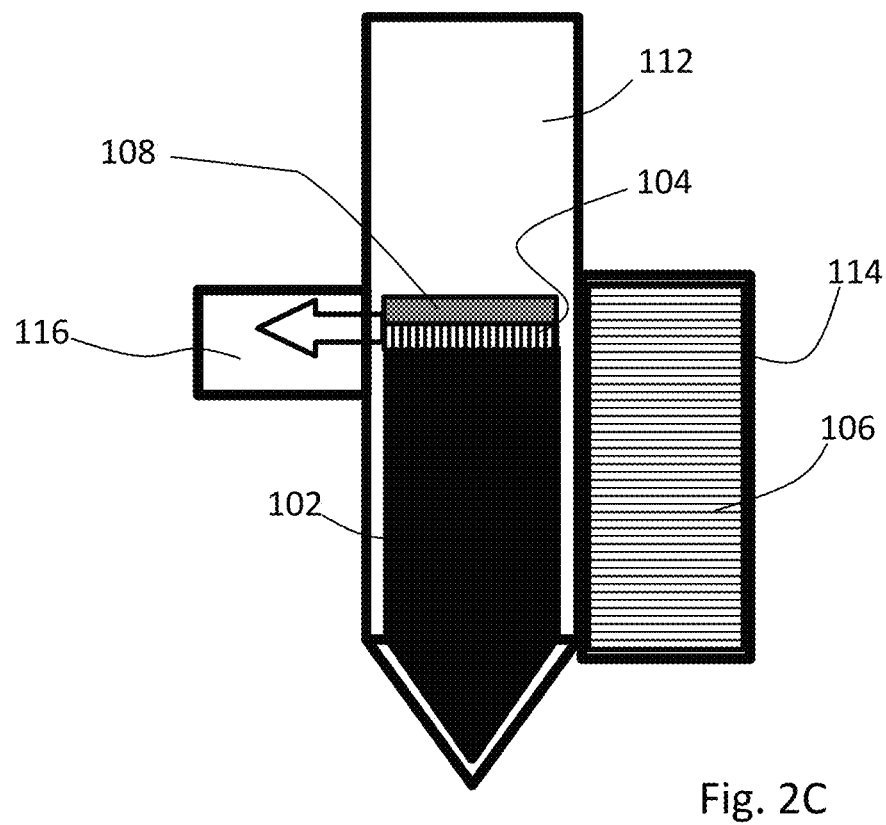

In use, the centrifuge tube 110 is centrifuged as described above to separate the bone marrow aspirate into layers, as illustrated in FIG. 2A. A second centrifuge run is performed to decant the serum layer 106 into the secondary chamber 114 as illustrated in FIG. 2B. A third centrifuge run performed in an upright position may then eject the adipose LS 108 and the buffy coat 104 into the tertiary chamber 116.

Figure 4:
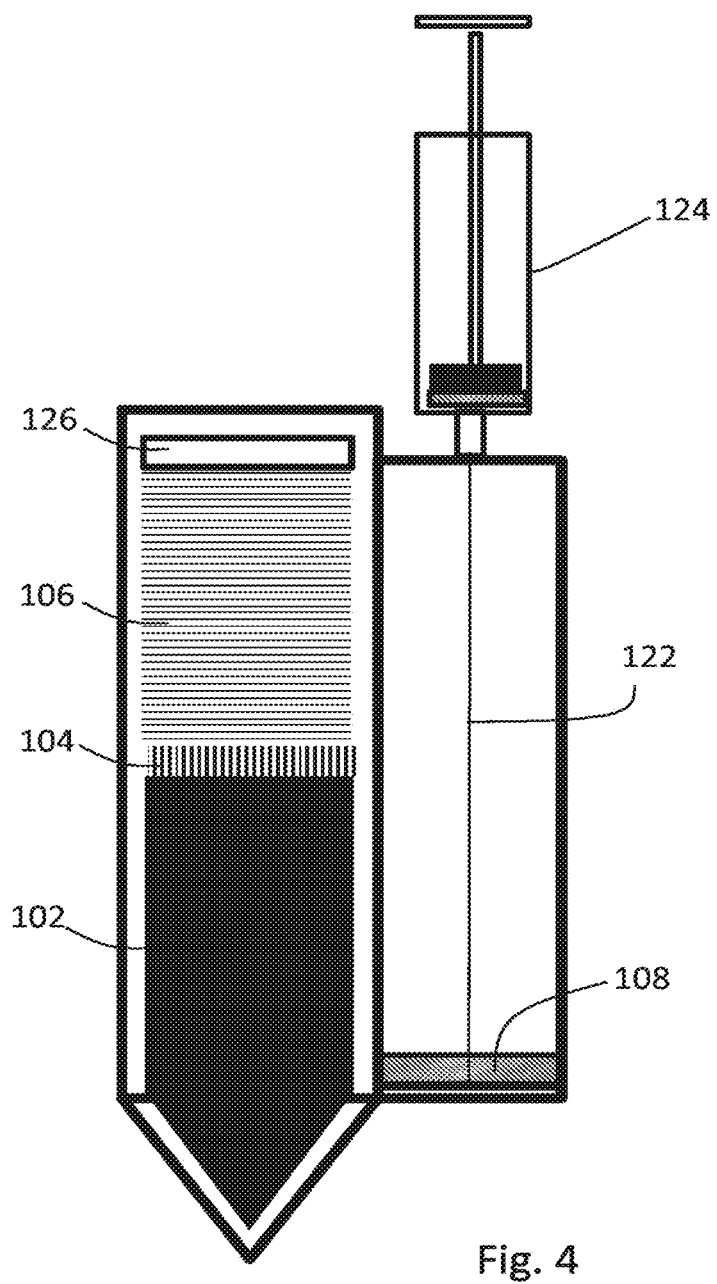
FIG. 4 is a schematic diagram of another embodiment of device useful for the collection, isolation and/or processing of the adipose supernatant layer of a bone marrow aspirate.

An alternative device embodiment is illustrated in FIGS. 3-4. In this alternative embodiment, certain layers, for example the adipose LS 108, serum 106, and buffy coat 104 are collected in the secondary chamber 114 of a dual chamber centrifuge tube 110 and then the adipose LS 108 (with or without the buffy coat) is isolated via the insertion of a tube, catheter, or needle 122, into the secondary chamber 114 such that the serum layer between the adipose LS and buffy coat is collected or drawn into a withdrawal chamber 124 which can be, but is not limited to a conventional syringe. The serum 106 can then be expelled from the withdrawal chamber 124 and the same chamber 124 can be used to collect the adipose LS 108 and/or buffy coat 104 or a fourth chamber can be used for adipose LS or buffy coat collection. As shown in FIGS. 3A, 3B. 3C and 4, a density-tuned floating element 126 may be used to cause the adipose LS (or other layers, depending on the density of the density-tuned floating element 126) to collect in the secondary chamber 114 for efficient withdrawal. The use of density-tuned floating elements 126 is described in more detail below.

With respect to the embodiment of FIGS. 3A, 3B, and 3C a first centrifuge run can be performed to fractionate the bone marrow aspirate as described above. Then, as shown in FIG. 3A, a second centrifuge run (performed with or without the addition of a density tuned floating element 126 to the centrifuge tube 110) may separate the buffy coat layer 104, serum layer 106, and adipose LS 108 in the secondary chamber 114. As shown in FIG. 3B, the serum layer 106 positioned between the adipose LS 108 and buffy coat layer 104 may be withdrawn into the withdrawal chamber 124. This step may be followed by withdraw of the valuable adipose LS 108 and buffy coat layer 104 as shown in FIG. 3C.

Figure 5:
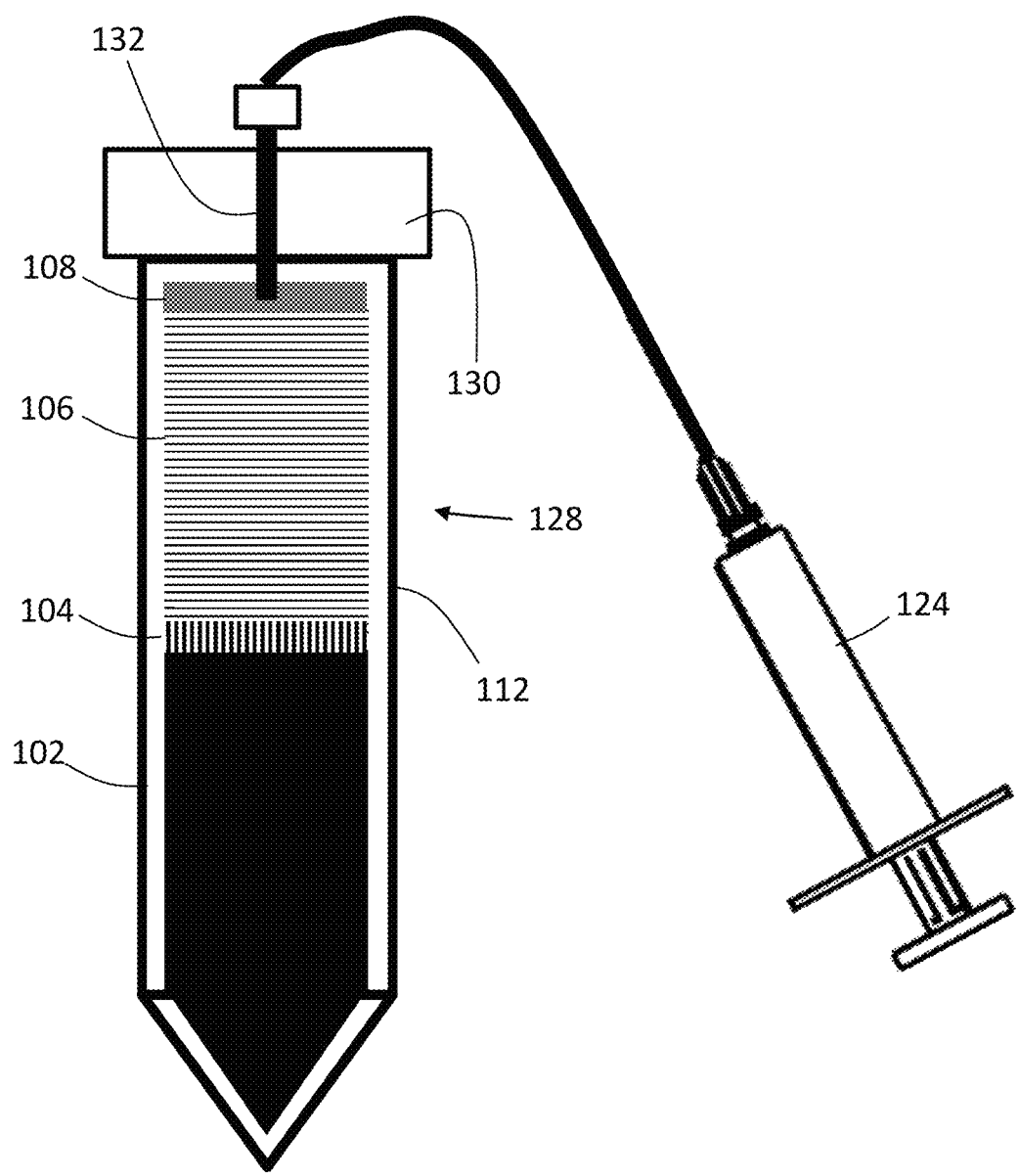
FIG. 5 is a schematic diagram of another embodiment of device useful for the collection, isolation and/or processing of the adipose supernatant layer of a bone marrow aspirate.

In an alternative device embodiment, as shown in FIG. 5, after the initial centrifuge run as described above, the centrifuge tube 128 is provided with a novel cap 130 supporting a tube 132 inserted to the correct depth to collect the adipose LS 108 from the centrifuge tube 128. Thus, the adipose LS 108 may be withdrawn into a withdraw chamber 124. The withdraw chamber 124 may be a syringe, later used for direct injection of the adipose LS 108 for therapeutic purposes, connected to the centrifuge chamber 128 by a Luer lock or otherwise firmly attached to the tube 132. The depth of the tube 132 may, in certain embodiments, be manually or automatically adjusted to the correct depth to optimize adipose LS 108 recovery.

In yet another device embodiment as shown in FIGS. 6A, 6B, and 6C, a centrifuge tube 134 is provided with a plunger 136 (which may or may not be detachable). As shown in FIGS. 6A-6C, the plunger equipped centrifuge tube 134 may be used to expel the RBC fraction 102, the buffy coat 104, and serum 106 from the inferior end of the tube 134. This allows the adipose LS 108 to remain in the chamber 134. In certain embodiments the centrifuge tube 134 may be implemented with a suitably sized syringe that provides for direct clinical injection of the isolated adipose LS 108 into a patient with or without serum.

Figure 7A:
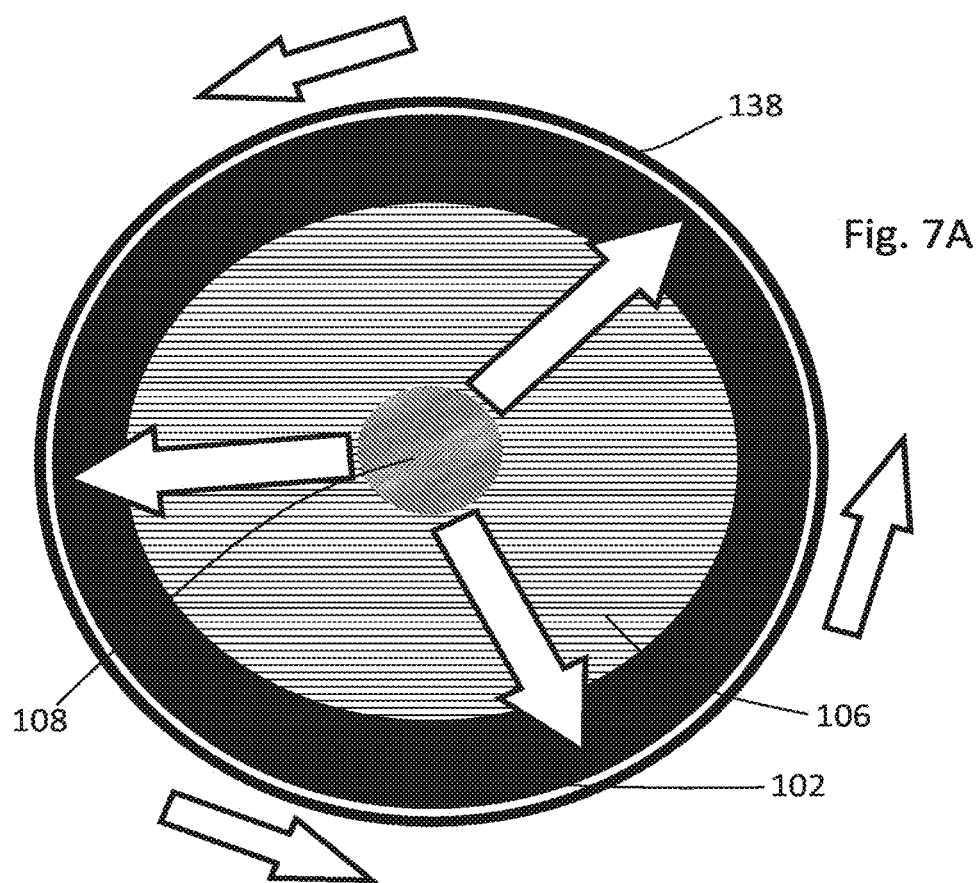
FIGS. 7A and 7B are schematic diagrams of another embodiment of device useful for the collection, isolation and/or processing of the adipose supernatant layer of a bone marrow aspirate.
Figure 7B:
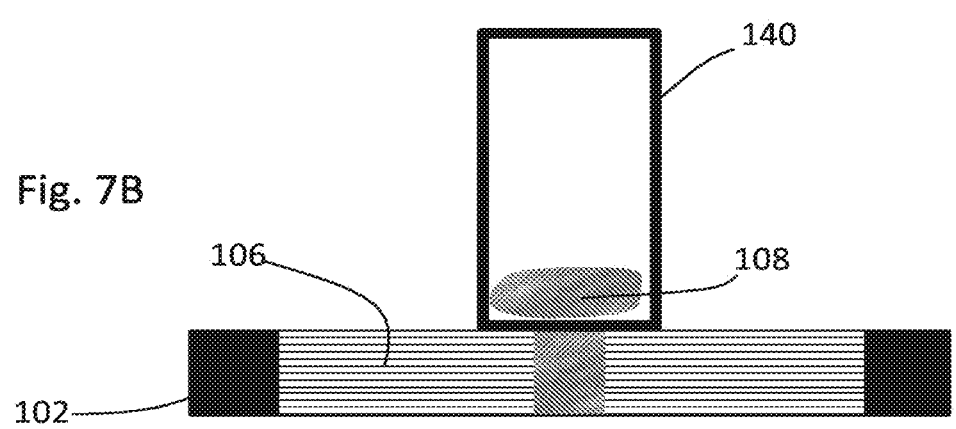
Figure 8B:
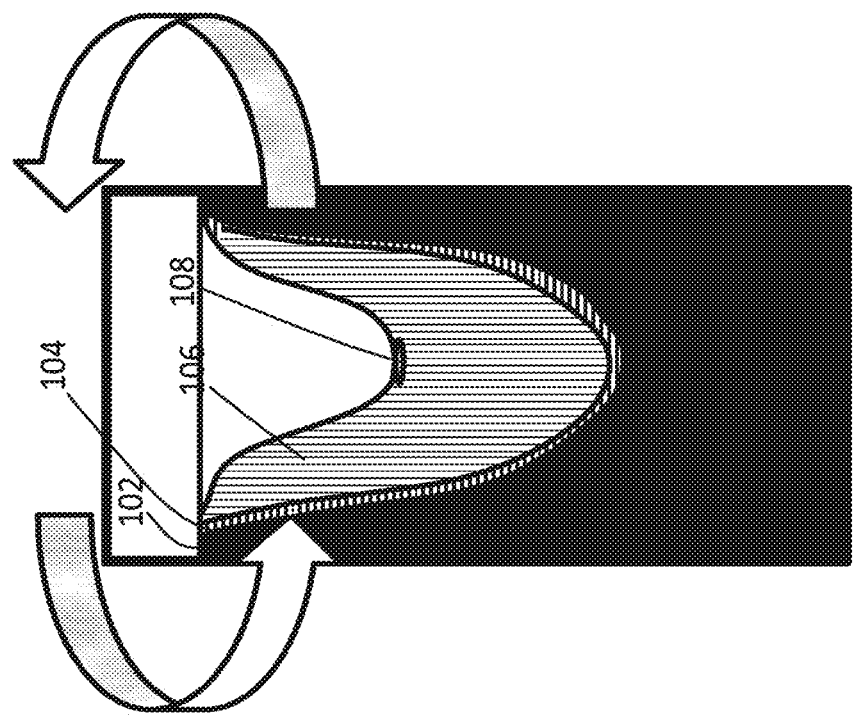
FIGS. 8A and 8B are schematic diagrams of another embodiment of device useful for the collection, isolation and/or processing of the adipose supernatant layer of a bone marrow aspirate.
Figure 8A:
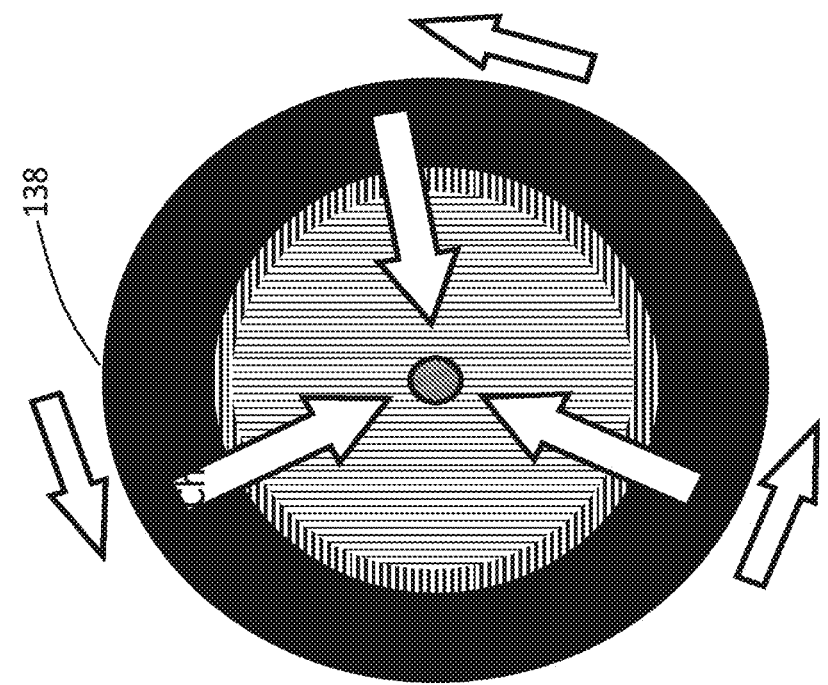

In the alternative embodiment of FIGS. 7A and 7B, a first chamber 138 is provided in the form of a disc that fractionates the whole marrow by spinning around a central axis. The adipose LS 108, being the least dense fraction, collects in the middle of the disc and may then be drawn off into a second, collection chamber 140 which may or may not be a syringe which would also provide for direct clinical use of the adipose LS 108. In certain embodiments, the collection chamber 140 may be connected to the first chamber 138 as shown in FIG. 7B. And opening or gate may be provided between the chambers 138, 140 such that the adipose LS 108 may be forced, expelled or otherwise drawn into the chamber 140 during the fractionation process. A similar embodiment, illustrated in FIGS. 8A and 8B, includes a first vertical separation tube 142 that rotates about its vertical axis causing a fractioning pattern as described above with the additional creation of a fluid meniscus where the adipose LS 108 in isolated in the center of a depression. The adipose LS may then be isolated and withdrawn using any of the methods described above.

Figures 9A, 9B:
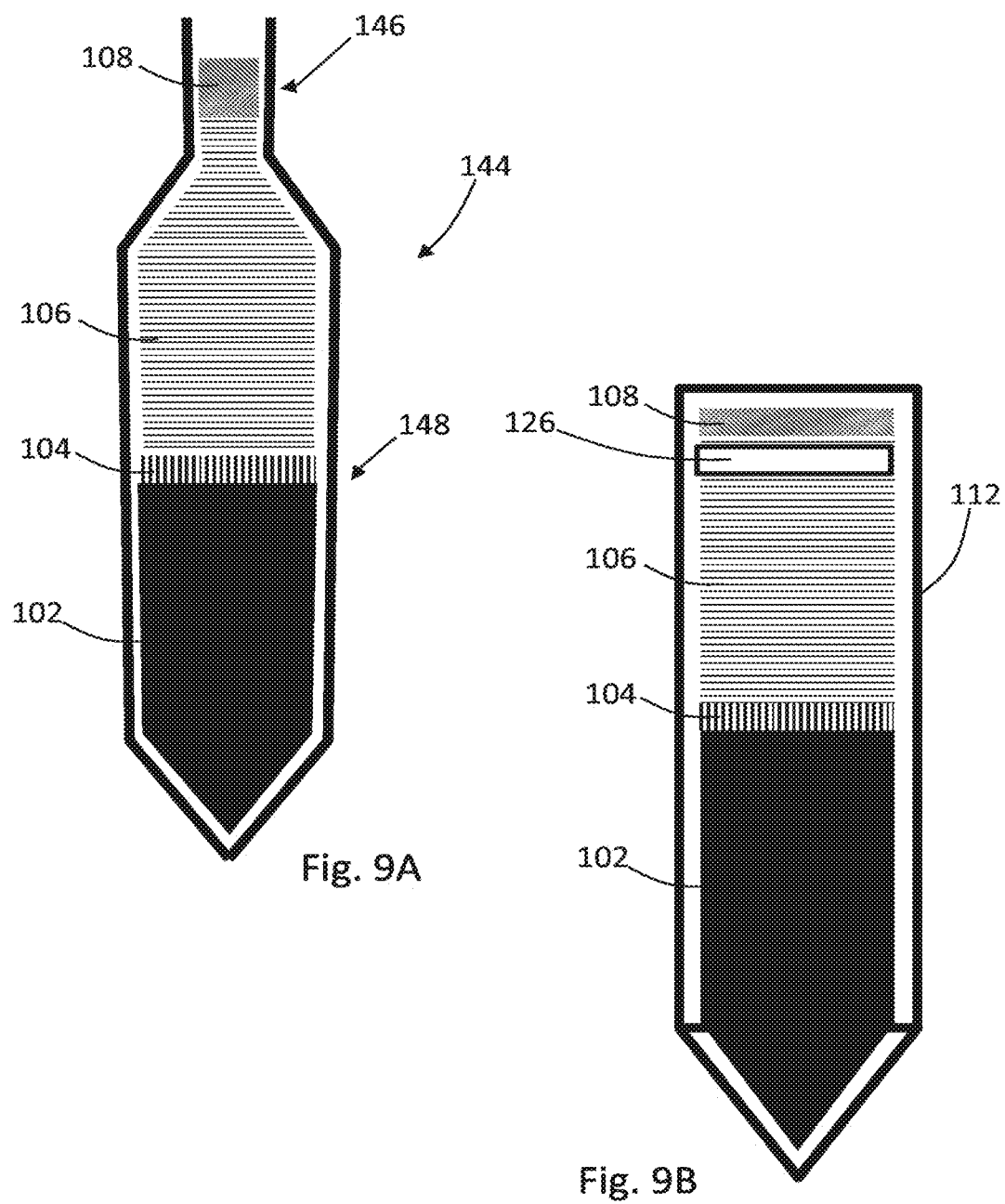
FIGS. 9A and 9B are schematic diagrams of two alternative embodiments of device useful for the collection, isolation and/or processing of the adipose supernatant layer of a bone marrow aspirate.
Figure 10:
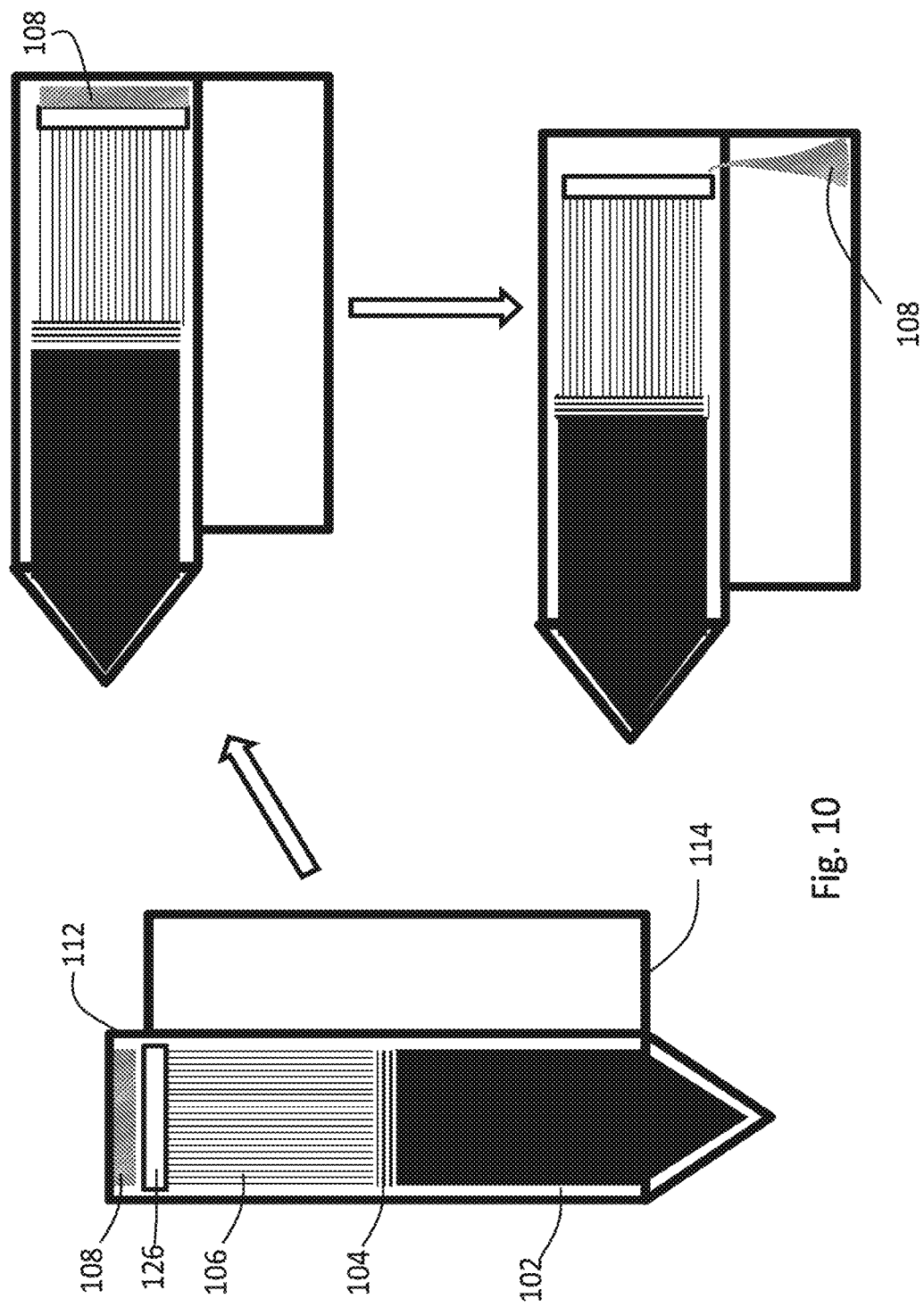
FIG. 10 is a schematic diagram of another embodiment of device useful for the collection, isolation and/or processing of the adipose supernatant layer of a bone marrow aspirate.

FIGS. 9A, 9B, and 10 illustrate alternative types of centrifuge tube suitable for use with certain embodiments described above. For example the centrifuge tube of FIG. 9A is implemented as a specialized tubular chamber 144 including a superior portion 146 which is restricted in diameter relative to the inferior portion 148. This configuration allows the superior adipose LS layer 108 to be elongated after fractionation for easier manual or automatic removal. This system may be part of a closed system providing for direct therapeutic use of the adipose LS 108, once isolated or part of an open system where the adipose LS 108 is for the process before therapeutic use.

In yet another centrifuge tube embodiment (FIG. 9B), a specially fabricated density-tuned floating disc 126 is provided having a selected specific gravity that causes the disc 126 to float just below the adipose LS 108 and above the serum 106 after fractionation, allowing for easier manual or automatic removal of the adipose LS 108. In a similar embodiment illustrated in FIG. 10, a two-chambered centrifuge tube 110 utilizes the specific gravity or density-tuned disc 126 to act as a stopper that can be affixed to the side walls of the primary chamber 112 of the centrifuge tube 110 after the disc 126 floats just above the serum layer 106 and below the adipose LS 108. The adipose LS 108 can then be manually or automatically decanted into a secondary chamber 114 for isolation.

Figure 11:
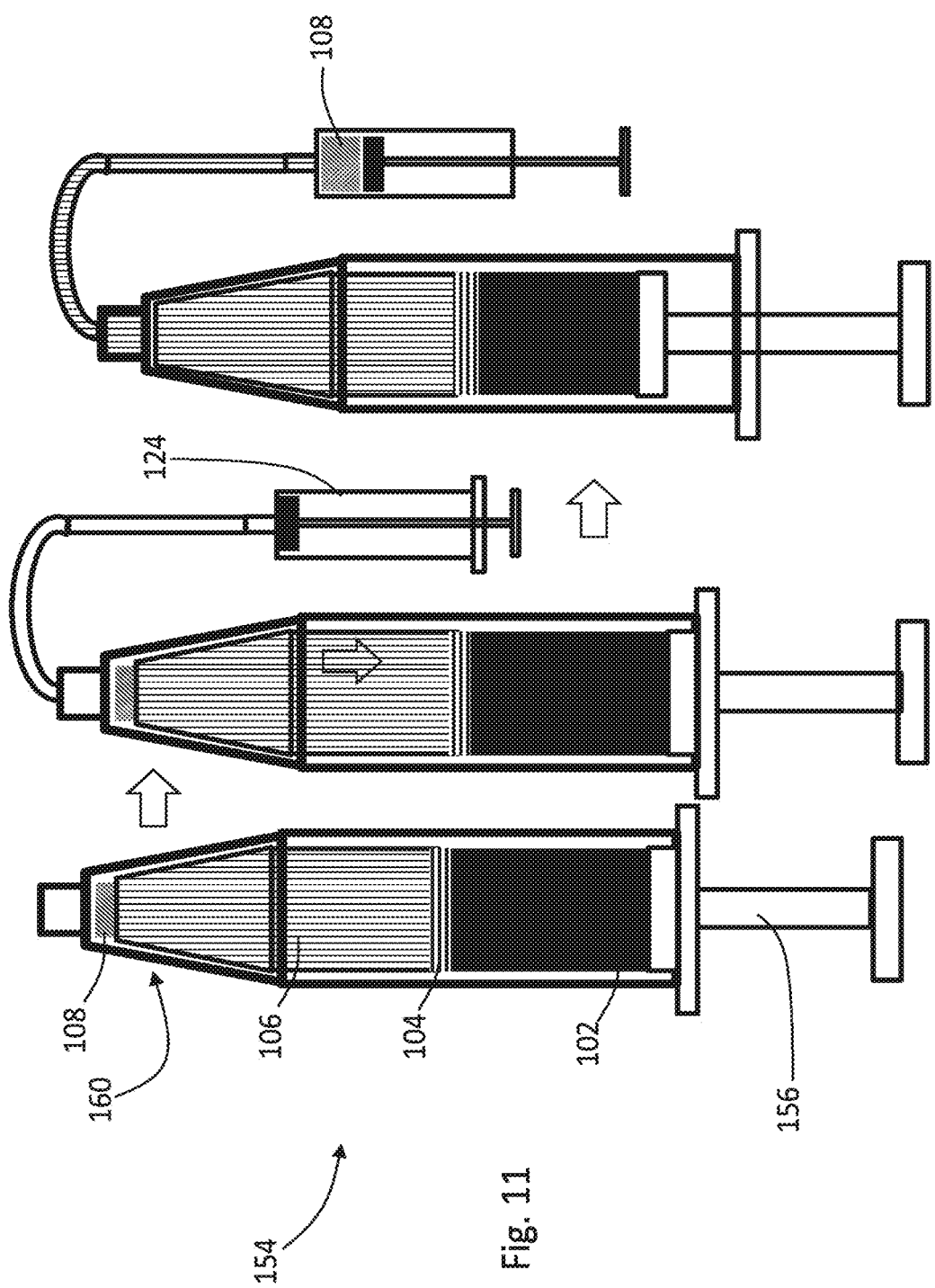
FIG. 11 is a schematic diagram of another embodiment of device useful for the collection, isolation and/or processing of the adipose supernatant layer of a bone marrow aspirate.

In an alternative device embodiment illustrated in FIG. 11, the centrifuge tube is implemented as a superiorly tapered tube 154 with an inferior plunger 156. The superiorly tapered tube 154 is attached directly, or via a tube 158, to a withdraw chamber 124. The superior tapered portion 160 of the tube 154 provides for the adipose LS 108 to be elongated and selectively pushed via the inferior plunger 156 or drawn through suction into the withdraw chamber 124 for isolation. Each tube or chamber 154, 124 may in certain embodiments be implemented as a syringe providing for the direct closed loop clinical use of the adipose LS 108.

In an alternative device embodiment illustrated in FIG. 12, the centrifuge tube 110 is implemented with a cap 130 on the superior end and a highly lipophilic porous membrane 168 positioned at or near the superior end of the 130. In use, a port and withdrawal tube 170 may be connected to a withdraw chamber, possibly implemented as a syringe or a vacuum line such that the adipose LS 108 may be lifted out of the fractionated solution opposite the porous highly lipophilic membrane 168.

Figure 14:
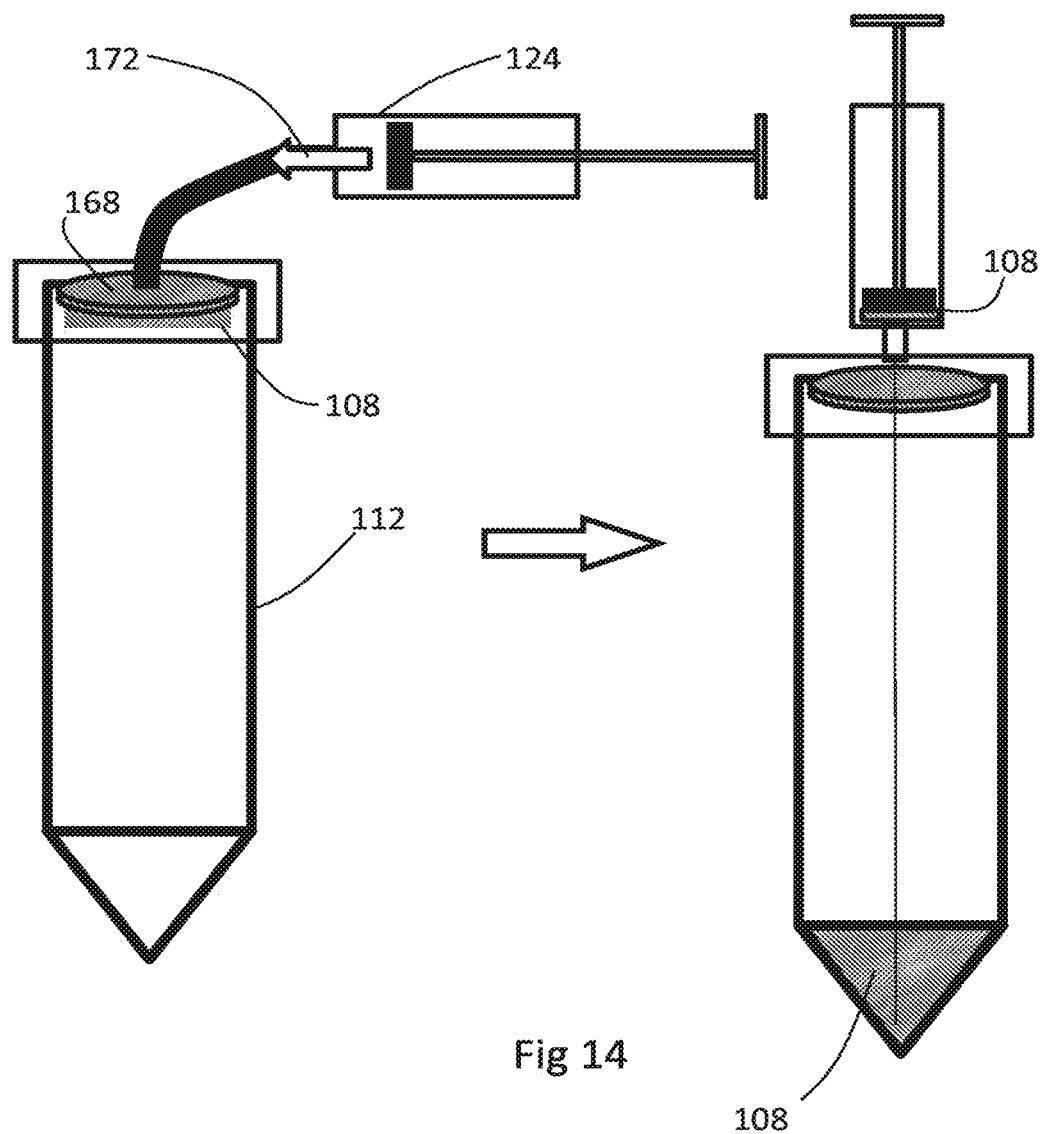
FIG. 14 is a schematic diagram of another embodiment of device useful for the collection, isolation and/or processing of the adipose supernatant layer of a bone marrow aspirate.

Optionally, as shown in FIG. 13 saline 172 or another biologically inert fluid may be added to the centrifuge tube 110 to float the adipose LS 108 and lift the adipose LS 108 into contact with the lipophilic membrane 168. Then, as shown in FIG. 14, the lipophilic membrane 168 can then be washed to displace the adipose LS 108 into an empty tube 110 where the adipose LS 108 may be collected by withdraw into a withdraw chamber 124 which may be implemented with a syringe providing for the direct clinical use of the adipose LS 108.

Figure 15:
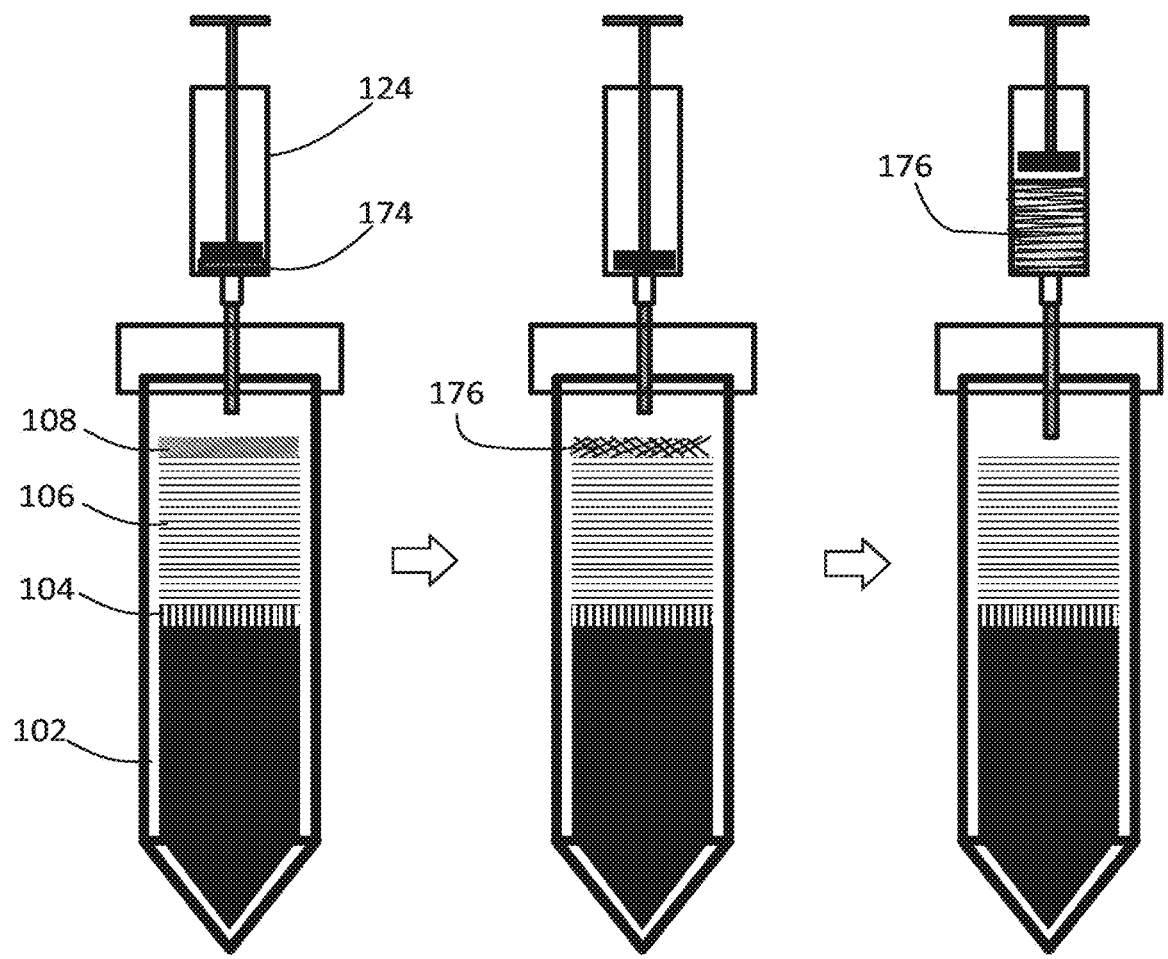
FIG. 15 is a schematic diagram of another embodiment of device useful for the collection, isolation and/or processing of the adipose supernatant layer of a bone marrow aspirate.

In another device embodiment illustrated in FIG. 15, the adipose LS 108 (which can optionally be intermixed slightly with the fibrinogen rich serum 106) is polymerized via the addition of thrombin, $CaCl_2$, or another clotting agent 174. Then the polymerized adipose LS 176 is either manually or automatically removed from the top of the serum layer or drawn though a tube into a withdrawal chamber 124.

Figure 16:
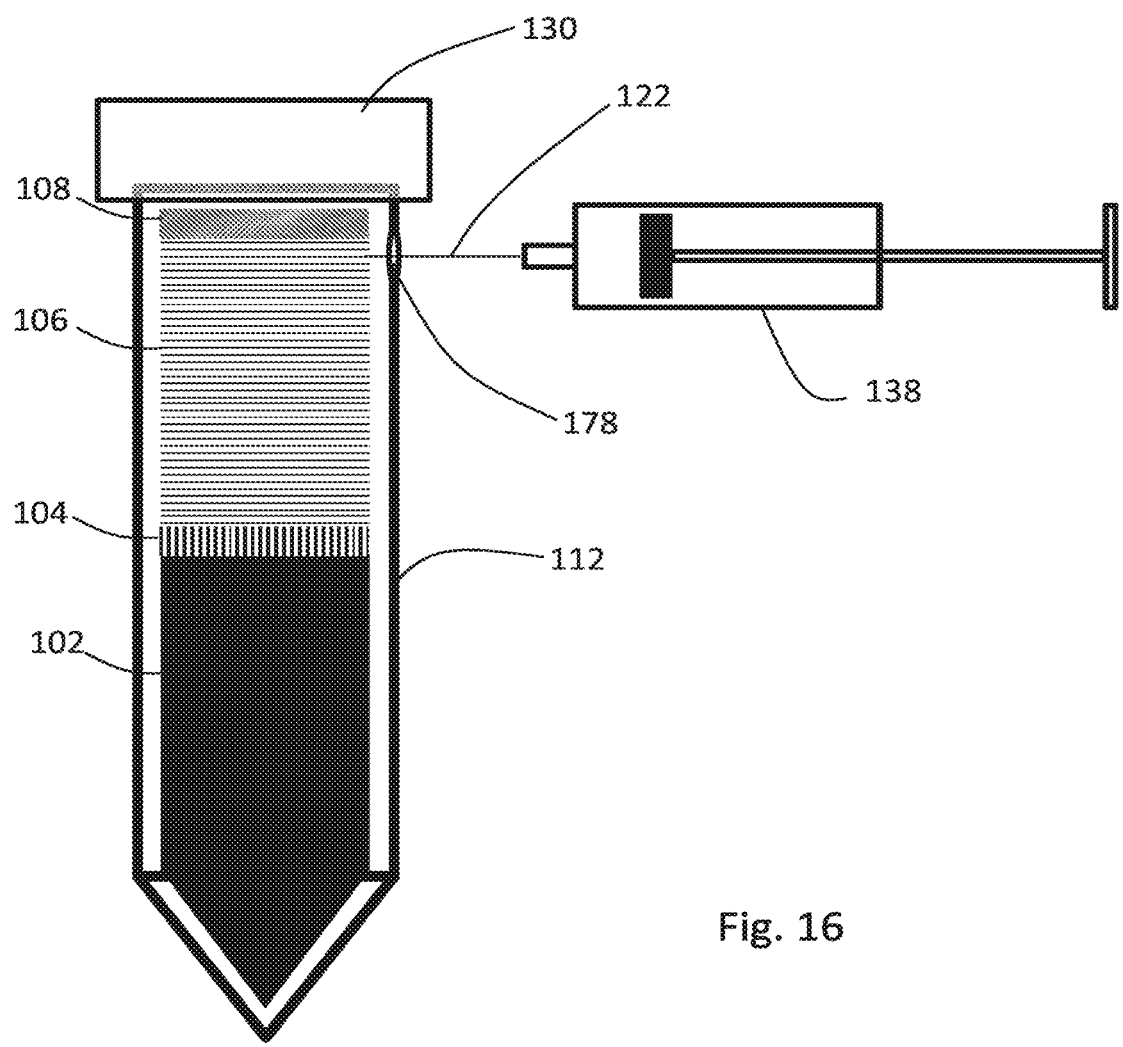
FIG. 16 is a schematic diagram of another embodiment of device useful for the collection, isolation and/or processing of the adipose supernatant layer of a bone marrow aspirate.

In yet another device embodiment illustrated in FIG. 16, the centrifuge tube 110 is provided with a side port 178 or multiple side ports that can be attached to or be punctured by a needle 122 or other conduit that connects to a withdraw chamber 124 which may be implemented with a syringe. The side port 178 or side ports are located at or just below the adipose LS 108 boundary such that the adipose LS can be drawn into the withdraw chamber 124 for isolation after fractionation.

Figures 17A, 17B, 17C:
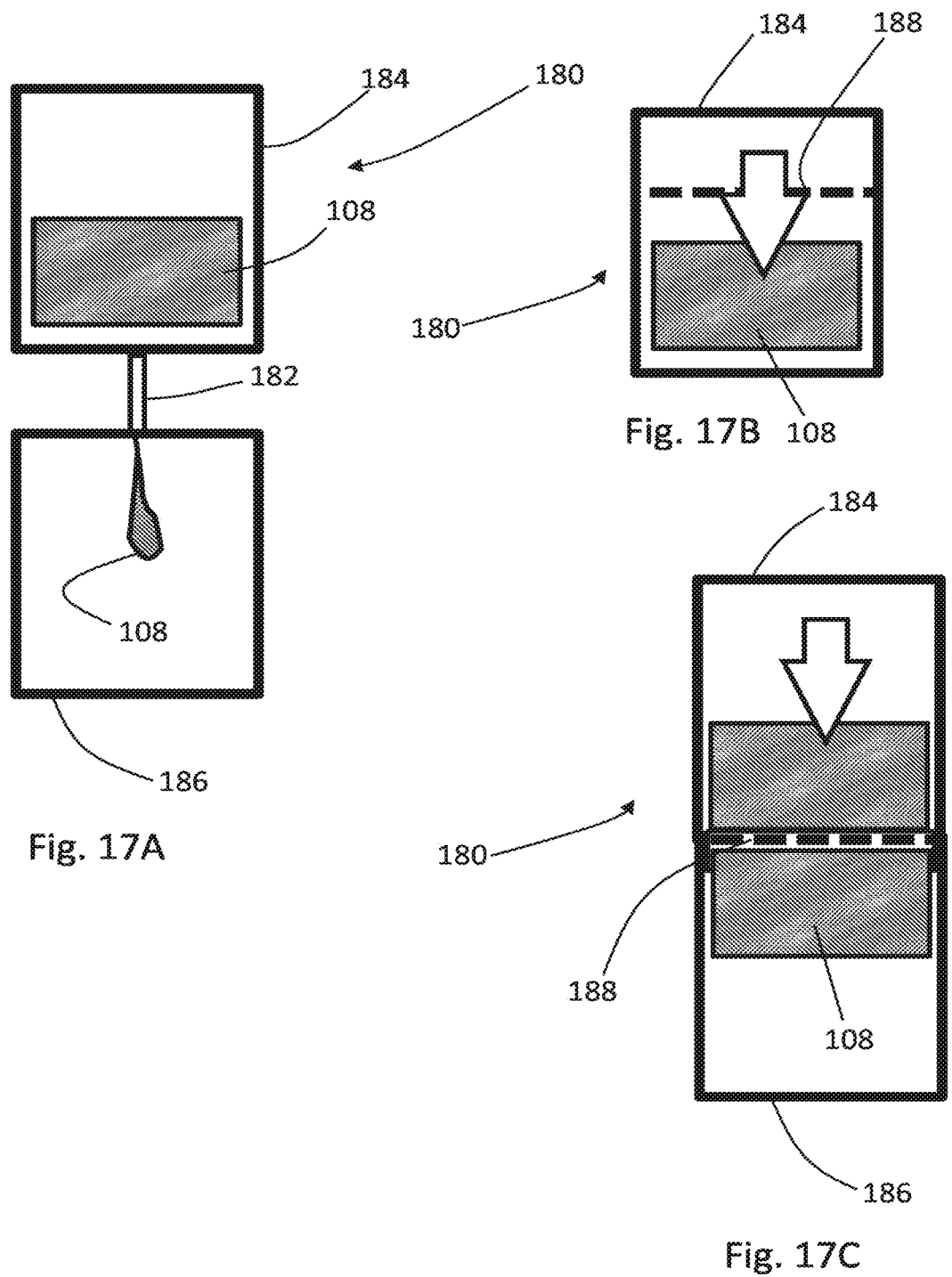
FIGS. 17A, 17B, and 17C are schematic diagrams of another embodiment of device useful for the collection, isolation and/or processing of the adipose supernatant layer of a bone marrow aspirate.

In any of the above described embodiments the device may also contain an integrated or separate well system that allows the isolated adipose LS to be processed such that the stem cells and other cellular components are separated from the fine collagen matrix present in the adipose tissue. Emulsification may be accomplished by mechanical or chemical means. For example, as shown in FIG. 17A, an emulsification system 180 may be provided as one or more additional chambers associated with the device or may be located in a separate apparatus such as a syringe providing for clinical use with a patient. In one representative, but non-limiting embodiment, the emulsification system 108 may use two or more chambers or a single chamber to accomplish emulsification processing. For example, emulsification may occur as the adipose LS 108 is forced through a small aperture 182 between a first emulsification chamber 184 and the second emulsification chamber 186. The adipose LS 108 may be forced repeatedly through the aperture 182 to accomplish the desired degree of emulsification.

Alternatively, as shown in FIGS. 17B and 17C a fine emulsification grate 188 may be located in one chamber and physically passed through the isolated adipose LS 108 (FIG. 17B). Alternatively, the adipose LS tissue may be passed from one chamber to another through an emulsification grate 188. Alternatively, the grate may be fixed with the adipose LS 108 passing from one part of a single chamber to another part of the same chamber.

In alternative device embodiments, the adipose LS can be processed in any one of the above described chambers or an out board vessel with a digestion agent such as collagenase or lecithin to dissociate the cells from the collagen matrix of the adipose LS 108. In other embodiments, the adipose LS can be processed using sonic energy or vibration to dissociate the cellular components.

In other alternative device embodiments, the dissociated cells plus the remaining adipose LS structural tissue (collagen and oils) can be further centrifuged to isolate a cell pellet that can then be washed. This pellet can then be added to the isolated bone marrow serum, platelets, RBCs, buffy coat, mesenchymal stem cells, other adult stem cells, or a nucleated cell mixture and/or isolated nucleated cell types for clinical use.

Alternative embodiments disclosed herein include methods of processing bone marrow aspirates and/or methods of collecting, preparing or reintroducing mesenchymal stem cells into an animal or human patient. Method embodiments include collecting bone marrow aspirate and fractionating the bone marrow aspirate to cause the formation of at least an adipose layer supernatant 108. The adipose layer supernatant may then be isolated utilizing one or more of the devices described above or similar devices suitable for isolating the adipose layer supernatant. For example, the bone marrow aspirate may be centrifuged to cause fractionation and the adipose layer supernatant withdrawn or decanted according to the techniques described above, or other suitable techniques.

The methods may further include processing the adipose layer to collect MSCs. For example, the adipose layer may be emulsified, mechanically emulsified, chemically digested, polymerized, subjected to sonic or vibrational energy, centrifuged or otherwise treated to aid with the extraction or collection of MSC's from the adipose layer tissue or fluid.

Upon collection, the adipose layer supernatant 108 or MSCs collected therefrom may be reintroduced into an animal or human patient to achieve therapeutic goals. In certain embodiments, bone marrow may be drawn; an adipose layer supernatant 108 collected and MSCs may be extracted therefrom and reintroduced into the patient in a single closed-loop treatment session. Alternatively, MSCs or adipose layer supernatant may be collected and stored or processed for subsequent use. For example MSCs collected and isolated as described herein may be expanded in culture prior to reintroduction into a patient for therapeutic purposes.

EXAMPLES

The following examples are provided for illustrative purposes only and are not intended to limit the scope of the invention. As noted above, applicants have been able to collect surprisingly high quantities of MSCs from bone marrow-derived adipose tissue when compared to the quantity of MSC's collected from similarly obtained buffy coat tissue. The results of preliminary laboratory investigations are described below and graphically represented in FIGS. 18-23.

Example 1

10 cc of bone marrow aspirate was withdrawn from several patients. Following a brief centrifugation step of the whole bone marrow aspirate in a sterile conical tube at 200×g, the buoyant adipose layer was collected manually via serological pipette along with a portion of bone marrow aspirate serum. In an initial plating of this bone marrow fraction, a 'dirty' culture consisting of cell debris and 'oily' substances in the native lipid layer was observed. These components were difficult to remove in later media changes.

Further, subsequent re-plating of the media containing lipid suspension resulted in the establishment of large numbers of fibroblast-like morphologies in cells believed to be MSCs. This indicated that the initial plating was sub-optimal and potentially resulted in discarding target cells, if not re-plated, thereby consuming additional resources and time.

Example 2

10 cc of bone marrow aspirate was withdrawn from seven patients. The adipose-plasma solution was passed through a small gauge emulsifier several times to dissociate adipose cells from the associated MSCs. This preparation was used for cell counting, flow cytometric analysis and in vitro plating for cell expansion.

Emulsification was employed in an effort to distort the lipid layer matrix to increase initial plating efficiency. Emulsification and plating resulted in an apparent increase of adherent cells compared to those not emulsified derived from the same lipid sample (see Example 1). In addition, re-plating of the supernatant following 2 days in culture did not result in the establishment of cells of the appropriate morphology and the initial culture was easily cleaned of the features described in the native layer. Therefore, mechanical disruption of the lipid layer via emulsification is believed to be optimal for initial in vitro plating of the lipid layer, potentially by exposing suspected MSCs to the environment and allowing for adhesion.

Figure 18:
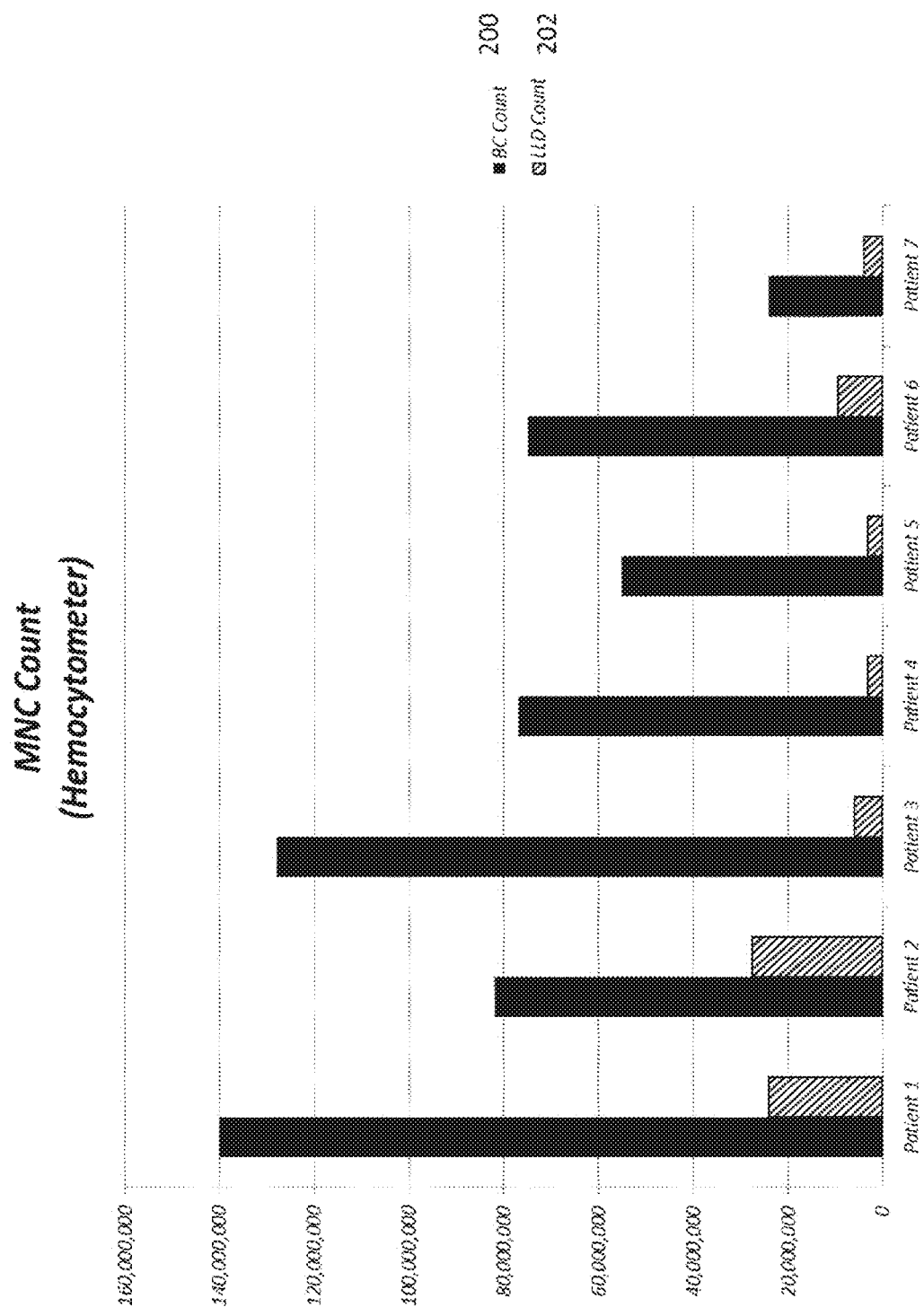
FIG. 18 is a graphic representation of data showing the manual count of mononucleated cells per 10 cc of bone marrow aspirate for all cells obtained from the buffy coat and the adipose supernatant layer.
Figure 19:
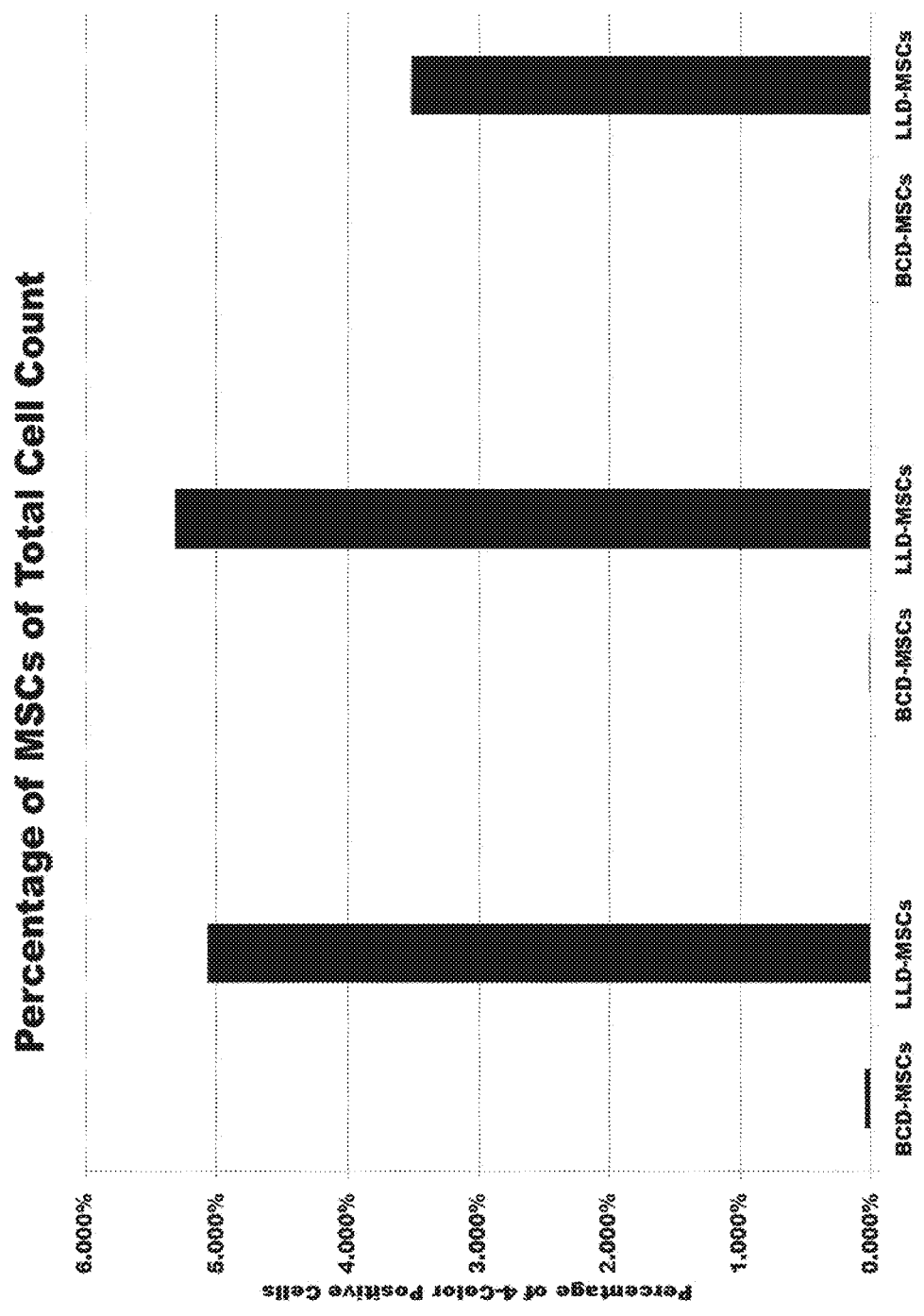
FIG. 19 is a graphic representation of flow cytometry data showing the percentage of MSCs to total cell count for MCSs obtained from the buffy coat and the adipose supernatant layer.

A very significant difference in the number and percentage of cells that stained positive for the stem cell markers CD44, CD73, CD90 and CD105 was observed when comparing isolations from the buffy coat with the adipose layer. For example, FIG. 18 illustrates the results of a manual cell count for 7 patients and indicates a lower mononucleated cell count (MNC) in the adipose layer (graph bars 200) compared to the buffy coat layer (graph bars 202). However, when compared to the contaminating cell background, as shown in FIG. 19, the adipose layer after emulsification demonstrated MSCs to comprise approximately 5% of the total cell population (graph bars 204). On the contrary, the buffy coat includes only 0.01-0.001% MSCs as determined by flow cytometry analysis (graph bars 206).

Figure 20:
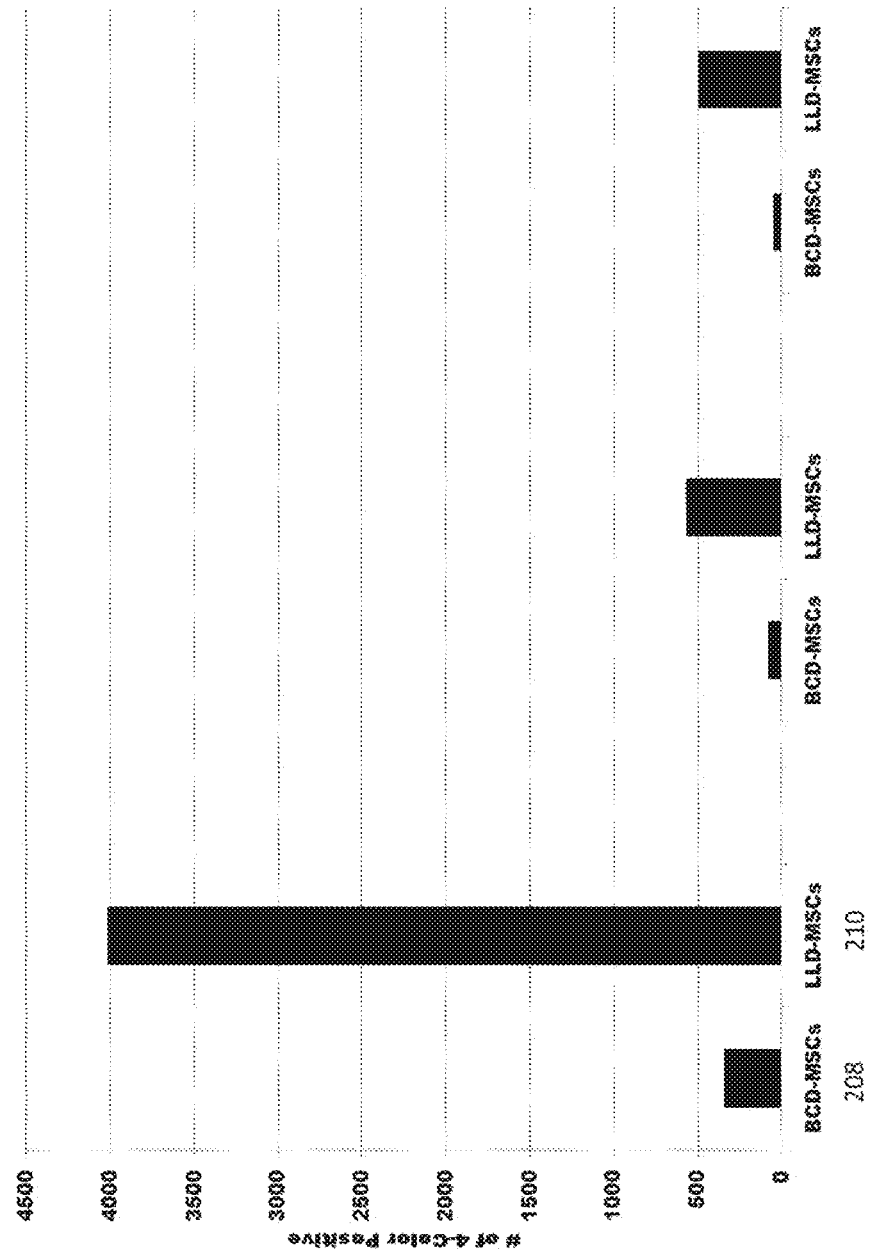
FIG. 20 is a graphic representation of data showing the gross quantity of MSCs per 10 cc of bone marrow aspirate for MCSs obtained from the buffy coat and the adipose supernatant layer.

Further, as shown in FIG. 20, the gross MSC count obtained from the buffy coat (graph bars 208) ranged from approximately 50-300 cells per 10 cc of bone marrow; while the gross MSC count obtained from the adipose layer collected and processed as described above (graph bars 210) was determined to range from approximately 500-4000 cells per 10 cc of bone marrow.

Accordingly, the number of non-MSC 'contaminating cells' in the buffy coat layer of bone marrow is significant higher than in the adipose layer; the percentage of MSCs in the buffy coat typically ranges from 0.01-0.001% as compared to the adipose layer where the range appears to be between 3%-15%. Based upon the data represented in FIGS. 19 and 20, it is believed that the number of MSCs in the adipose layer far exceeds that of the buffy coat layer due to the large difference in the percentage of MSCs that exist in the respective regions.

Figure 21:
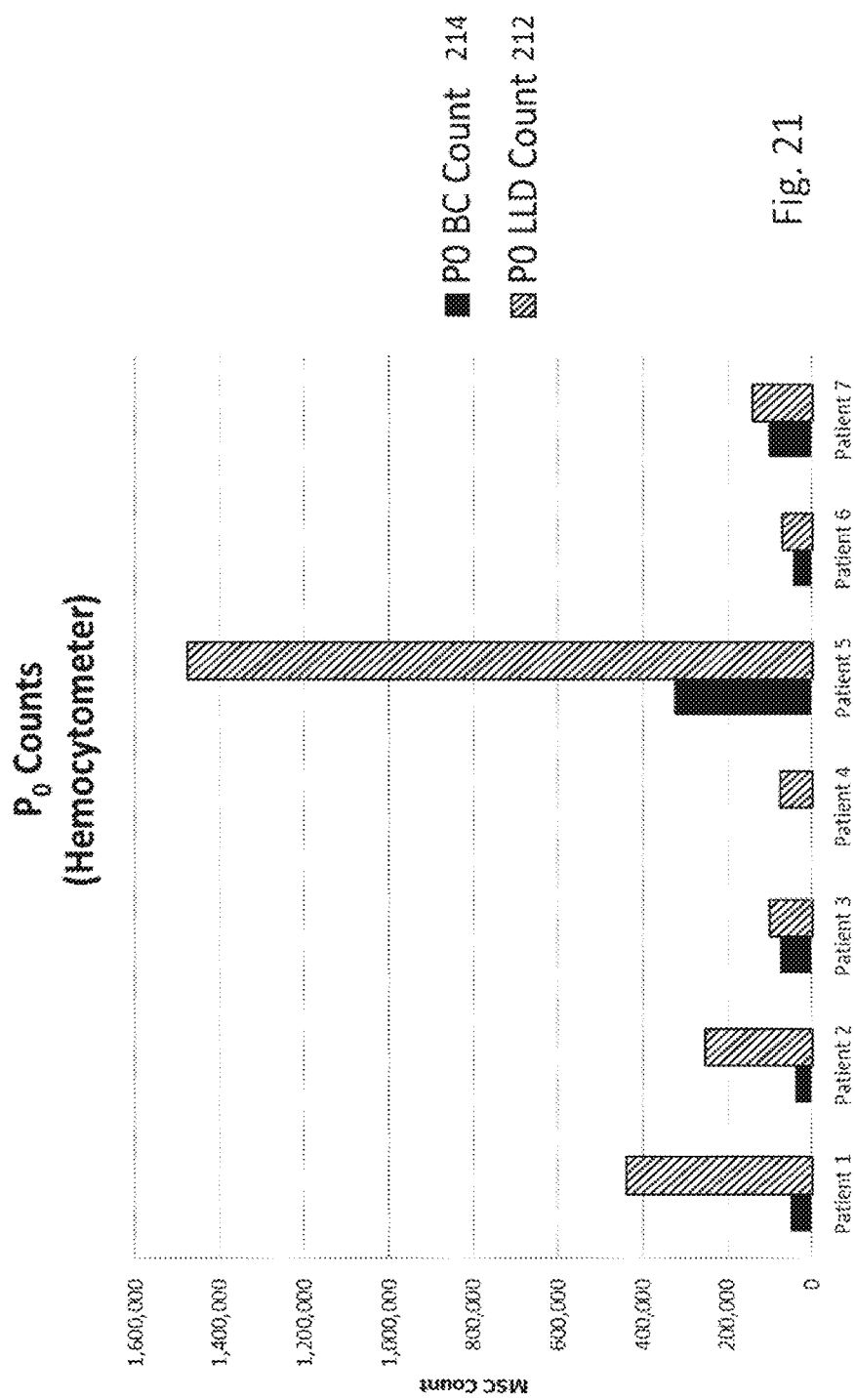
FIG. 21 is a graphic representation of data showing the number of MSCs initially obtained from 10c.c. of bone marrow from both the buffy coat and lipid layer fractions.
Figure 22:
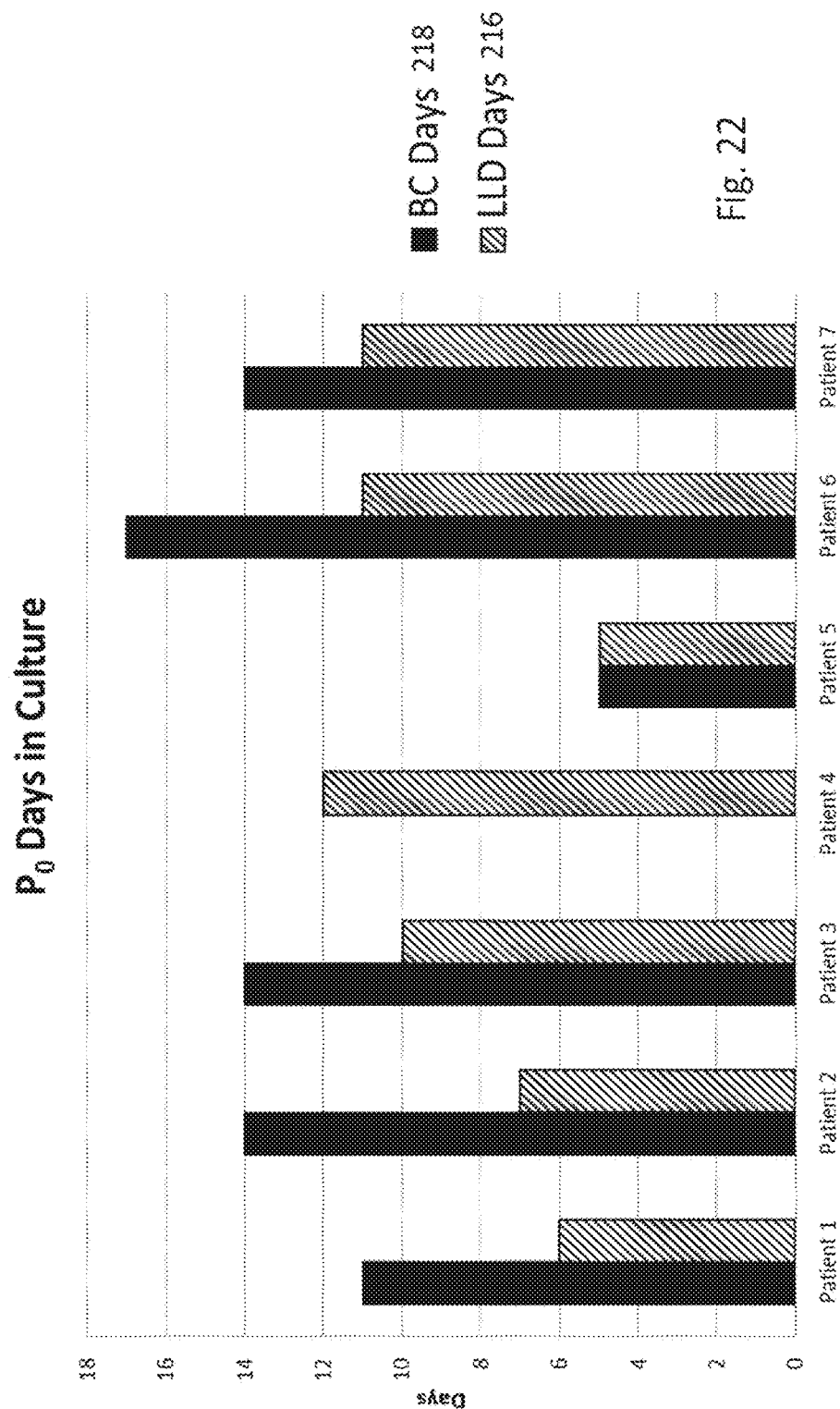
FIG. 22 is a graphic representation of data showing the number of days in culture required to obtain the quantity of adipose and buffy coat MSCs derived from 10c.c. bone marrow necessary to passage.

As shown in FIGS. 21-23, in vitro studies confirmed that elevated levels of MSCs can be obtained from the bone marrow adipose layer after processing bone marrow aspirate with the devices and methods described herein versus comparable levels of buffy coat derived MSCs. FIG. 21 depicts the number of MSCs expanded ex vivo from 10 cc. of bone marrow derived adipose tissue (graph bars 212) versus the number of MSCs expanded ex vivo from 10 cc. of bone marrow derived buffy coat layer (graph bars 214). This data supports the foregoing flow cytometric data of FIGS. 19 and 20) and it is clear that a significantly larger number of MSCs were expanded from the adipose layer compared to the buffy coat layer using the methods described.

As shown in FIG. 23, additional passages revealed that adipose derived MSCs (graph bars 222) are also characterized by a lower doubling time resulting from increased rate of division when compared to buffy coat derived MSCs seeded at the same cell density (graph bars 220). This indicates that the innate rate of division differs between the adipose derived and buffy coat derived MSCs, suggesting therapeutic advantages from the adipose derived MSCs.

As shown in FIG. 23, additional passages revealed that adipose derived MSCs (graph bars 220) are also characterized by a lower doubling time resulting from increased rate of division when compared to buffy coat derived MSCs seeded at the same cell density (graph bars 222). This indicates that the innate rate of division differs between the adipose derived and buffy coat derived MSCs, suggesting therapeutic advantages from the adipose derived MSCs.

Example 3

Bone marrow aspirate samples were withdrawn from three patients and divided into equal volume subsamples to investigate the effect of emulsification. One subsample from each patient was emulsified as described herein. A 2nd subsample was not emulsified. The cells were plated in a T-25 flask and grown in a 10% FBS/90% DMEM growth medium for 6 days. As shown in FIGS. 24-25, for each patient, the cells from the emulsified culture (graph bars 224) initiate and proliferate faster when compared to cells grown from the non-emulsified culture. In addition, the cell cultures prepared from emulsified samples were observed to be cleaner and more easily cleared of debris with passage. Thus, the non-emulsified samples appeared "dirty" for longer periods of time.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

The description of the various embodiments has been presented for purposes of illustration and description, but is not intended to be exhaustive or limiting of the embodiments to the form disclosed. The scope of the present disclosure is limited only by the scope of the following claims. Many modifications and variations will be apparent to those of ordinary skill in the art. The embodiments described and shown in the figures were chosen and described in order to best explain the principles of the disclosed embodiments, the practical application, and to enable others of ordinary skill in the art to understand the various embodiments with various modifications as are suited to the particular use contemplated.

The description of the various embodiments has been presented for purposes of illustration and description, but is not intended to be exhaustive or limiting of the embodiments to the form disclosed. The scope of the present disclosure is limited only by the scope of the following claims. Many modifications and variations will be apparent to those of ordinary skill in the art. The embodiments described and shown in the figures was chosen and described in order to best explain the principles of the disclosed embodiments, the practical application, and to enable others of ordinary skill in the art to understand the various embodiments with various modifications as are suited to the particular use contemplated.

What is claimed is:

1. A fluid processing device comprising:
   a first chamber comprising a first sidewall, and a first upper opening;
   a second chamber adjacent to the first chamber, the second chamber comprising a second sidewall, and a second upper opening;
   an opening through the first sidewall and second sidewall, said opening defining a fluid pathway from the first chamber to the second chamber; and
   a mechanical emulsification system in fluid communication with the second chamber for emulsifying a liquid contained in the second chamber,
   wherein a portion of the first sidewall and a portion of the second sidewall define a shared sidewall, wherein a first surface of the shared sidewall is a vertical inner surface of the first chamber and a second surface of the shared sidewall is a vertical inner surface of the second chamber,
   wherein the opening extends through the shared sidewall from the first surface to the second surface.

2. The fluid processing device of claim 1 wherein the opening is positioned at an upper edge of the second sidewall.

3. The fluid processing device of claim 1 wherein one of the first upper opening and the second upper opening comprises a connector configured to connect to a syringe.

4. The fluid processing device of claim 3 wherein both of the first upper opening and the second upper opening comprises the connector configured to connect with the syringe.

5. The fluid processing device of claim 3 further comprising the syringe selectively connectable to one of the first upper opening and the second upper opening.

6. The fluid processing device of claim 1 further comprising a density tuned float received in the first chamber.

7. The fluid processing device of claim 6, wherein the density tuned float received in the first chamber affixes to the first sidewall of the first chamber after floating to a location based on one or more densities of a fluid contained in the fluid processing device.

8. The fluid processing device of claim 1, wherein the second chamber comprises the mechanical emulsification system for emulsifying the liquid contained in the second chamber.

9. The fluid processing device of claim 8, wherein the mechanical emulsification system comprises an emulsification grate fixed to the second sidewall.

10. A method for processing a fluid comprising:
    providing a device, the device comprising;
    a first chamber comprising a first sidewall, and a first upper opening;
    a second chamber adjacent to the first chamber, the second chamber comprising a second sidewall, and a second upper opening;
    an opening through the first sidewall and second sidewall, said opening defining a fluid pathway from the first chamber to the second chamber; and
    a mechanical emulsification system in fluid communication with the second chamber for emulsifying a liquid contained in the second chamber,
    wherein a portion of the first sidewall and a portion of the second sidewall define a shared sidewall, wherein a first surface of the shared sidewall is a vertical inner surface of the first chamber and a second surface of the shared sidewall is a vertical inner surface of the second chamber,
  wherein the opening extends through the shared sidewall from the first surface to the second surface;
placing the fluid into the first chamber;
centrifuging the fluid in the first chamber to separate the fluid into fluid fractions;
decanting one or more fluid fractions from the first chamber into the second chamber through the opening while leaving one or more fluid fractions in the first chamber;
re-centrifuging the fluid fractions in the first and second chambers; and
removing one or more fluid fractions from at least one of the first chamber and the second chamber.

11. The method of claim 10 wherein the fluid is a bone marrow aspirate.

12. The method of claim 10 further comprising:
positioning the opening at an upper edge of the first sidewall; and
decanting one or more less-dense fluid fractions through the opening.

13. The method of claim 10 further comprising:
providing one of the first upper opening and the second upper opening with a connector configured to connect to a syringe;
connecting a syringe to the connector; and
removing the one or more fluid fractions from at least one of the first chamber and the second chamber with the syringe.

14. The method of claim 10 further comprising:
providing a density tuned float in the first chamber; and
separating at least one less-dense fluid fraction from one or more remaining fluid fractions with the density tuned float.

* * * * *